(12) United States Patent
Dachs, II

(10) Patent No.: US 12,097,006 B2
(45) Date of Patent: Sep. 24, 2024

(54) LATCH RELEASE FOR SURGICAL INSTRUMENT

(71) Applicant: INTUITIVE SURGICAL OPERATIONS, INC., Sunnyvale, CA (US)

(72) Inventor: Gregory W. Dachs, II, San Mateo, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 79 days.

(21) Appl. No.: 17/848,030

(22) Filed: Jun. 23, 2022

(65) Prior Publication Data
US 2022/0361975 A1 Nov. 17, 2022

Related U.S. Application Data

(63) Continuation of application No. 16/282,164, filed on Feb. 21, 2019, now Pat. No. 11,389,259, which is a
(Continued)

(51) Int. Cl.
*A61B 5/00* (2006.01)
*A61B 1/00* (2006.01)
(Continued)

(52) U.S. Cl.
CPC .......... *A61B 46/10* (2016.02); *A61B 1/00142* (2013.01); *A61B 17/00234* (2013.01);
(Continued)

(58) Field of Classification Search
CPC ................ A61B 46/10; A61B 1/00142; A61B 17/00234; A61B 34/30; A61B 34/35;
(Continued)

(56) References Cited

U.S. PATENT DOCUMENTS 4,386,933 A 6/1983 Sanchez
4,542,272 A 9/1985 Hubbard et al.
(Continued)

FOREIGN PATENT DOCUMENTS

CN 1631622 A 6/2005
CN 101203344 A 6/2008
(Continued)

OTHER PUBLICATIONS

Extended European Search Report for Application No. EP22169553.9, mailed on Jul. 18, 2022, 09 pages.
(Continued)

*Primary Examiner* — May A Abouelela
(74) *Attorney, Agent, or Firm* — JONES ROBB, PLLC

(57) ABSTRACT

A medical instrument comprises an instrument control surface configured to mate with an instrument sterile adapter to receive input drive forces through the sterile adapter to control actuation of the surgical instrument, the instrument control surface comprising a first opening defined in the instrument control surface. A latch structure of the instrument comprises a locking surface configured to engage a latch arm in response to the latch arm being received in the opening, wherein in an engaged state of the latch arm with the locking surface the medical instrument is attached to the instrument sterile adapter and the latch structure prevents movement of the latch arm in a first direction. A latch release is moveable in the engaged state of the latch arm with the locking surface to exert a force causing movement of the latch arm in a second direction to disengage the latch arm from the locking surface.

20 Claims, 13 Drawing Sheets

Related U.S. Application Data continuation of application No. 14/660,834, filed on Mar. 17, 2015, now Pat. No. 10,213,268.

(60) Provisional application No. 62/104,306, filed on Jan. 16, 2015, provisional application No. 62/103,991, filed on Jan. 15, 2015, provisional application No. 62/019,318, filed on Jun. 30, 2014, provisional application No. 61/954,502, filed on Mar. 17, 2014, provisional application No. 61/954,497, filed on Mar. 17, 2014, provisional application No. 61/954,571, filed on Mar. 17, 2014, provisional application No. 61/954,557, filed on Mar. 17, 2014, provisional application No. 61/954,595, filed on Mar. 17, 2014.

(51) Int. Cl.
*A61B 17/00* (2006.01)
*A61B 34/00* (2016.01)
*A61B 34/30* (2016.01)
*A61B 34/35* (2016.01)
*A61B 34/37* (2016.01)
*A61B 46/00* (2016.01)
*A61B 46/10* (2016.01)
*A61B 90/00* (2016.01)
*A61B 90/98* (2016.01)
*A61B 18/00* (2006.01)
*A61B 46/23* (2016.01)
*F16H 1/20* (2006.01)

(52) U.S. Cl.
CPC ............ *A61B 34/30* (2016.02); *A61B 34/35* (2016.02); *A61B 34/37* (2016.02); *A61B 34/70* (2016.02); *A61B 46/40* (2016.02); *A61B 90/08* (2016.02); *A61B 90/361* (2016.02); *A61B 90/98* (2016.02); *A61B 2017/00477* (2013.01); *A61B 2018/00172* (2013.01); *A61B 46/23* (2016.02); *A61B 2090/0813* (2016.02); *F16H 1/20* (2013.01); *Y10T 29/49817* (2015.01); *Y10T 403/59* (2015.01)

(58) Field of Classification Search
CPC ......... A61B 34/37; A61B 34/70; A61B 46/40; A61B 90/08; A61B 90/361; A61B 90/98; A61B 46/23; A61B 2017/00477; A61B 2018/00172; A61B 2090/0813; F16H 1/20; Y10T 29/49817; Y10T 403/59
See application file for complete search history.

(56) References Cited

U.S. PATENT DOCUMENTS

| | | | |
|---|---|---|---|
| 5,069,221 A | 12/1991 | Smith et al. | |
| 5,214,573 A | 5/1993 | Roza | |
| 5,469,863 A | 11/1995 | Shah | |
| 5,679,423 A | 10/1997 | Shah | |
| 5,803,086 A | 9/1998 | Scholz et al. | |
| 6,331,181 B1 | 12/2001 | Tierney et al. | |
| 6,471,172 B1 | 10/2002 | Lemke et al. | |
| 7,096,870 B2 | 8/2006 | Lamprich et al. | |
| 7,125,403 B2* | 10/2006 | Julian | A61B 34/76 606/1 |
| 7,758,569 B2* | 7/2010 | Brock | A61B 17/00234 606/1 |
| 7,947,050 B2 | 5/2011 | Lee et al. | |
| 7,963,913 B2 | 6/2011 | Devengenzo et al. | |
| 8,220,468 B2 | 7/2012 | Cooper et al. | |
| 8,506,555 B2 | 8/2013 | Ruiz Morales | |
| 8,529,582 B2 | 9/2013 | Devengenzo et al. | |
| 8,555,892 B2 | 10/2013 | Traub | |
| 8,998,930 B2 | 4/2015 | Orban, III | |
| 9,096,033 B2 | 8/2015 | Holop et al. | |
| 9,687,312 B2 | 6/2017 | Dachs, II et al. | |
| 9,839,487 B2 | 12/2017 | Dachs, II et al. | |
| 10,022,193 B2 | 7/2018 | Cooper et al. | |
| 10,045,828 B2 | 8/2018 | Dachs, II et al. | |
| 10,213,268 B2 | 2/2019 | Dachs, II et al. | |
| 10,278,784 B2 | 5/2019 | Dachs, II | |
| 10,363,109 B2 | 7/2019 | Dachs, II et al. | |
| 10,420,622 B2 | 9/2019 | Dachs et al. | |
| 10,485,621 B2 | 11/2019 | Morrissette et al. | |
| 10,537,400 B2 | 1/2020 | Dachs, II et al. | |
| 10,543,051 B2 | 1/2020 | Schena et al. | |
| 10,595,836 B2 | 3/2020 | Smaby et al. | |
| 10,610,320 B2 | 4/2020 | Dachs, II et al. | |
| 10,639,119 B2 | 5/2020 | Dachs, II et al. | |
| 10,898,288 B2 | 1/2021 | Dachs, II et al. | |
| 10,912,616 B2 | 2/2021 | Dachs, II et al. | |
| 11,045,274 B2 | 6/2021 | Dachs, II et al. | |
| 11,389,259 B2 | 7/2022 | Dachs, II | |
| 11,446,105 B2 | 9/2022 | Dachs, II et al. | |
| 11,717,370 B2 | 8/2023 | Dachs, II | |
| 2002/0032452 A1 | 3/2002 | Tierney et al. | |
| 2002/0111635 A1 | 8/2002 | Jensen et al. | |
| 2002/0143319 A1 | 10/2002 | Brock | |
| 2003/0216723 A1 | 11/2003 | Shinmura et al. | |
| 2004/0049205 A1 | 3/2004 | Lee et al. | |
| 2005/0119527 A1 | 6/2005 | Banik et al. | |
| 2005/0234435 A1 | 10/2005 | Layer | |
| 2005/0240178 A1 | 10/2005 | Morley et al. | |
| 2005/0244217 A1 | 11/2005 | Burke et al. | |
| 2005/0251110 A1 | 11/2005 | Nixon | |
| 2006/0161138 A1 | 7/2006 | Orban et al. | |
| 2006/0235436 A1 | 10/2006 | Anderson et al. | |
| 2006/0260622 A1 | 11/2006 | Wooley et al. | |
| 2006/0273135 A1 | 12/2006 | Beetel | |
| 2007/0012135 A1 | 1/2007 | Tierney et al. | |
| 2007/0142825 A1 | 6/2007 | Prisco et al. | |
| 2007/0142971 A1 | 6/2007 | Schena | |
| 2008/0103491 A1 | 5/2008 | Omori et al. | |
| 2008/0140088 A1 | 6/2008 | Orban, III | |
| 2009/0248038 A1 | 10/2009 | Blumenkranz et al. | |
| 2009/0248039 A1 | 10/2009 | Cooper et al. | |
| 2010/0152566 A1 | 6/2010 | Rains et al. | |
| 2010/0163057 A1 | 7/2010 | Anderson et al. | |
| 2010/0170519 A1 | 7/2010 | Romo et al. | |
| 2010/0175701 A1 | 7/2010 | Reis et al. | |
| 2010/0234857 A1* | 9/2010 | Itkowitz | G09B 23/285 700/259 |
| 2011/0015650 A1 | 1/2011 | Choi et al. | |
| 2011/0084113 A1 | 4/2011 | Bedi et al. | |
| 2011/0118754 A1 | 5/2011 | Dachs, II et al. | |
| 2011/0213383 A1 | 9/2011 | Lee et al. | |
| 2011/0277776 A1 | 11/2011 | McGrogan et al. | |
| 2011/0288560 A1 | 11/2011 | Shohat et al. | |
| 2011/0290854 A1 | 12/2011 | Timm et al. | |
| 2011/0290855 A1* | 12/2011 | Moore | A61B 34/30 227/176.1 |
| 2011/0295270 A1 | 12/2011 | Giordano et al. | |
| 2011/0313477 A1 | 12/2011 | McLean et al. | |
| 2012/0150192 A1 | 6/2012 | Dachs, II et al. | |
| 2012/0197094 A1 | 8/2012 | Zhang et al. | |
| 2012/0247489 A1 | 10/2012 | Orban, III et al. | |
| 2012/0292367 A1 | 11/2012 | Morgan et al. | |
| 2013/0110129 A1 | 5/2013 | Reid et al. | |
| 2013/0211397 A1* | 8/2013 | Parihar | A61B 90/10 606/130 |
| 2013/0211401 A1 | 8/2013 | Bailey et al. | |
| 2013/0274062 A1 | 10/2013 | Arai et al. | |
| 2013/0274657 A1 | 10/2013 | Zirps et al. | |
| 2013/0325034 A1* | 12/2013 | Schena | A61B 34/30 606/130 |
| 2013/0331858 A1* | 12/2013 | Devengenzo | A61B 90/00 901/41 |
| 2014/0000411 A1 | 1/2014 | Shelton, IV et al. | |
| 2014/0001234 A1* | 1/2014 | Shelton, IV | A61B 17/072 74/25 |
| 2014/0001235 A1 | 1/2014 | Shelton, IV | |
| 2014/0005484 A1* | 1/2014 | Charles | A61B 17/00 600/201 |

(56) References Cited

U.S. PATENT DOCUMENTS

| | | | |
|---|---|---|---|
| 2014/0005677 A1* | 1/2014 | Shelton, IV | A61B 34/30 219/121.72 |
| 2014/0005718 A1* | 1/2014 | Shelton, IV | A61B 34/30 606/205 |
| 2014/0007886 A1 | 1/2014 | Singh et al. | |
| 2014/0066944 A1 | 3/2014 | Taylor et al. | |
| 2014/0069437 A1* | 3/2014 | Reis | A61B 34/30 128/852 |
| 2014/0277334 A1* | 9/2014 | Yu | A61B 34/30 901/30 |
| 2015/0223832 A1* | 8/2015 | Swaney | A61B 34/10 703/1 |
| 2016/0184037 A1 | 6/2016 | Cooper et al. | |
| 2018/0168752 A1 | 6/2018 | Scheib et al. | |
| 2019/0183596 A1 | 6/2019 | Dachs, II | |
| 2019/0254766 A1 | 8/2019 | Dachs, II | |
| 2019/0380803 A1 | 12/2019 | Dachs, II et al. | |
| 2020/0069389 A1 | 3/2020 | Morrissette et al. | |
| 2020/0155130 A1 | 5/2020 | Smaby et al. | |
| 2020/0222139 A1 | 7/2020 | Dachs, II et al. | |
| 2020/0229886 A1 | 7/2020 | Dachs, II et al. | |
| 2021/0137627 A1 | 5/2021 | Dachs, II et al. | |
| 2021/0196420 A1 | 7/2021 | Dachs, II et al. | |
| 2023/0320804 A1 | 10/2023 | Dachs, II | |

FOREIGN PATENT DOCUMENTS

| | | |
|---|---|---|
| CN | 101297267 A | 10/2008 |
| CN | 101443162 A | 5/2009 |
| CN | 101454092 A | 6/2009 |
| CN | 102630154 A | 8/2012 |
| CN | 102711635 A | 10/2012 |
| CN | 103038141 A | 4/2013 |
| CN | 203234838 U | 10/2013 |
| DE | 20015892 U1 | 1/2001 |
| DE | 102012008535 A1 | 10/2013 |
| DE | 102012013242 A1 | 1/2014 |
| EP | 1815950 A1 | 8/2007 |
| EP | 1862123 A2 | 12/2007 |
| EP | 1897511 A2 | 3/2008 |
| EP | 2259744 A1 | 12/2010 |
| EP | 2691043 A1 | 2/2014 |
| GB | 2538326 A | 11/2016 |
| JP | H0666326 A | 3/1994 |
| JP | H07163574 A | 6/1995 |
| JP | 2001187067 A | 7/2001 |
| JP | 2003325543 A | 11/2003 |
| JP | 2005505379 A | 2/2005 |
| JP | 2006511285 A | 4/2006 |
| JP | 2010022415 A | 2/2010 |
| JP | 2012050706 A | 3/2012 |
| JP | 2012210294 A | 11/2012 |
| JP | 2013502280 A | 1/2013 |
| JP | 2013034833 A | 2/2013 |
| JP | 2013034859 A | 2/2013 |
| KR | 20080100212 A | 11/2008 |
| KR | 20110032444 A | 3/2011 |
| KR | 20110036452 A | 4/2011 |
| KR | 20110095795 A | 8/2011 |
| KR | 20130080638 A | 7/2013 |
| KR | 20130120316 A | 11/2013 |
| WO | WO-9825666 A1 | 6/1998 |
| WO | WO-03032855 A1 | 4/2003 |
| WO | WO-2004060184 A1 | 7/2004 |
| WO | WO-2007075864 A1 | 7/2007 |
| WO | WO-2007095637 A1 | 8/2007 |
| WO | WO-2007111737 A2 | 10/2007 |
| WO | WO-2007126443 A2 | 11/2007 |
| WO | WO-2007142698 A2 | 12/2007 |
| WO | WO-2008101228 A2 | 8/2008 |
| WO | WO-2009123925 A1 | 10/2009 |
| WO | WO-2009151205 A1 | 12/2009 |
| WO | WO-2010117625 A2 | 10/2010 |
| WO | WO-2010126128 A1 | 11/2010 |
| WO | WO-2010126129 A1 | 11/2010 |
| WO | WO-2011037394 A2 | 3/2011 |
| WO | WO-2011143016 A1 | 11/2011 |
| WO | WO-2011143020 A1 | 11/2011 |
| WO | WO-2012158449 A1 | 11/2012 |
| WO | WO-2013018931 A1 | 2/2013 |
| WO | WO-2013181536 A1 | 12/2013 |
| WO | WO-2014004255 A1 | 1/2014 |
| WO | WO-2014005689 A2 | 1/2014 |
| WO | WO-2014035308 A1 | 3/2014 |
| WO | WO-2014035803 A1 | 3/2014 |
| WO | WO-2015023730 A1 | 2/2015 |
| WO | WO-2015142824 A1 | 9/2015 |

OTHER PUBLICATIONS

Extended European Search Report for Application No. 15765493.0, mailed on Jul. 28, 2017, 7 pages.
Extended European Search Report for Application No. 15765779.2, mailed on Jul. 18, 2017, 8 pages.
Extended European Search Report for Application No. 15766019.2, mailed on Oct. 20, 2017, 7 pages.
Extended European Search Report for Application No. 19181058.9 mailed on Aug. 22, 2019, 7 pages.
Extended European Search Report for Application No. EP15764089. 7, mailed on Oct. 25, 2017, 11 pages.
Extended European Search Report for Application No. EP15764268. 7, mailed on Nov. 6, 2017, 8 pages.
Extended European Search Report for Application No. EP15764610. 0, mailed on Nov. 23, 2017, 8 pages.
Extended European Search Report for Application No. EP15764745. 4, mailed on Oct. 30, 2017, 10 pages.
Extended European Search Report for Application No. EP15764881. 7, mailed on Nov. 30, 2017, 10 pages.
Extended European Search Report for Application No. EP15764940. 1, mailed on Oct. 30, 2017, 8 pages.
Extended European Search Report for Application No. EP19201778. 8, mailed on Nov. 27, 2019, 5 pages.
Extended European Search Report for Application No. EP20154204. 0, mailed on May 7, 2020, 7 pages.
Extended European Search Report for Application No. EP20154737. 9, mailed on Apr. 17, 2020, 10 pages.
Extended European Search Report for Application No. EP20159147. 6, mailed on Jun. 16, 2020, 7 pages.
Extended European Search Report for Application No. EP20161337. 9, mailed on May 7, 2020, 8 pages.
Extended European Search Report for Application No. EP20172196.6 mailed on Aug. 7, 2020, 8 pages.
International Search Report and Written Opinion for Application No. PCT/US15/20876, mailed on Jun. 12, 2015, 17 pages.
International Search Report and Written Opinion for Application No. PCT/US15/20880, mailed on Jul. 14, 2015, 9 pages.
International Search Report and Written Opinion for Application No. PCT/US15/20882, mailed on May 29, 2015, 14 pages.
International Search Report and Written Opinion for Application No. PCT/US15/20884, mailed on Jun. 12, 2015, 13 pages.
International Search Report and Written Opinion for Application No. PCT/US15/20885, mailed on Jun. 5, 2015, 7 pages.
International Search Report and Written Opinion for Application No. PCT/US15/20886, mailed on Jun. 4, 2015, 19 pages.
International Search Report and Written Opinion for Application No. PCT/US15/20888, mailed on Jun. 5, 2015, 9 pages.
International Search Report and Written Opinion for Application No. PCT/US15/21020, mailed on Jun. 5, 2015, 10 pages.
International Search Report and Written Opinion for Application No. PCT/US15/21111, mailed on May 21, 2015, 10 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

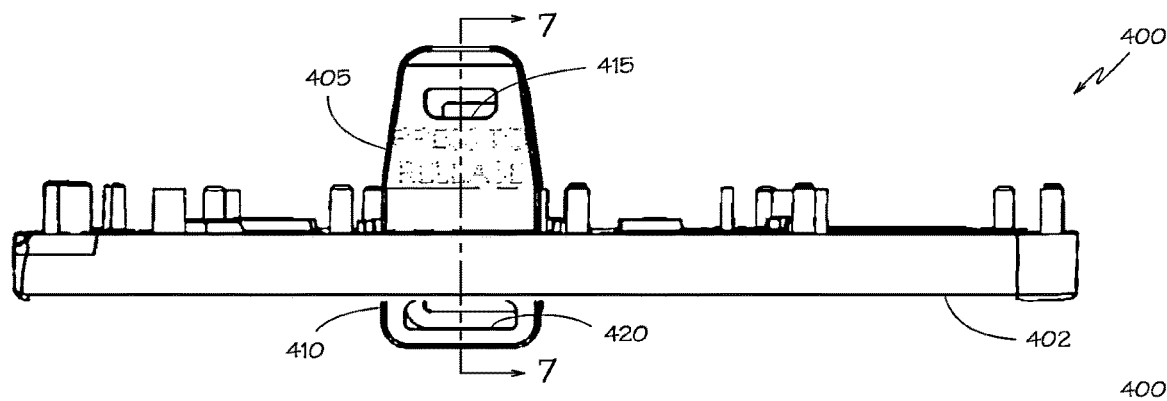
FIG. 6
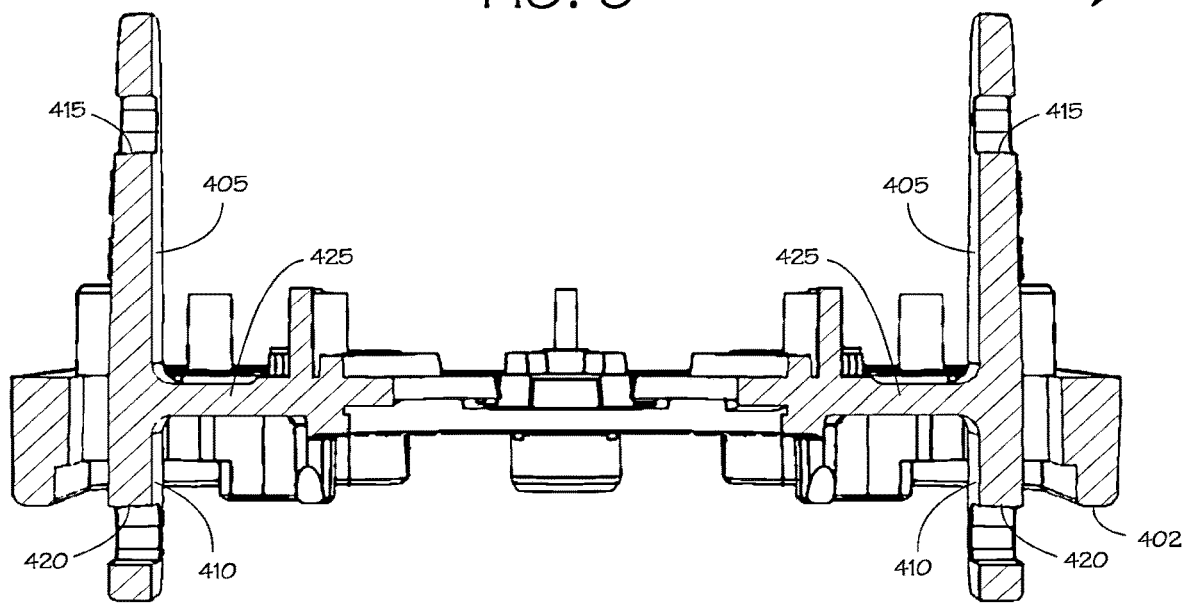
FIG. 7A
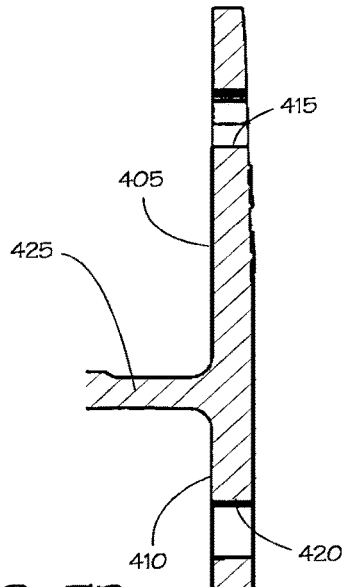 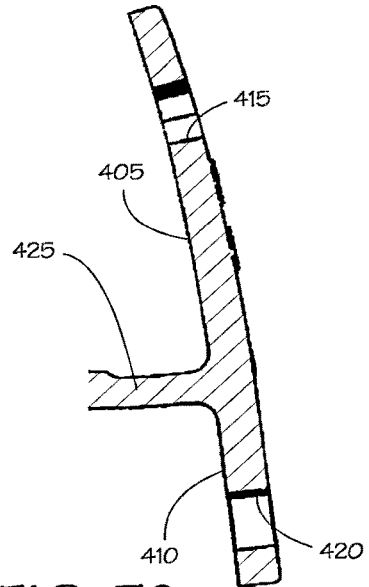
FIG. 7B  FIG. 7C

LATCH RELEASE FOR SURGICAL INSTRUMENT

CROSS REFERENCE TO RELATED APPLICATIONS

This application is a continuation of U.S. patent application Ser. No. 16/282,164, filed Feb. 21, 2019, which is a continuation of U.S. patent application Ser. No. 14/660,834, filed Mar. 17, 2015 (now U.S. Pat. No. 10,213,268), which claims the benefit pursuant to 35 U.S.C. 119(e) of U.S. Provisional Application No. 62/104,306, filed Jan. 16, 2015, U.S. Provisional Application No. 62/103,991, filed Jan. 15, 2015, U.S. Provisional Application No. 62/019,318, filed Jun. 30, 2014, U.S. Provisional Application No. 61/954,497, filed Mar. 17, 2014, U.S. Provisional Application No. 61/954,502, filed Mar. 17, 2014, U.S. Provisional Application No. 61/954,557, filed Mar. 17, 2014, U.S. Provisional Application No. 61/954,571, filed Mar. 17, 2014, U.S. Provisional Application No. 61/954,595, filed Mar. 17, 2014, and each of which applications is incorporated by reference herein in its entirety.

BACKGROUND

Field

Embodiments of the invention relate to the field of latches; and more specifically, to latch assemblies for coupling actuators to surgical instruments.

Background

Minimally invasive medical techniques have been used to reduce the amount of extraneous tissue which may be damaged during diagnostic or surgical procedures, thereby reducing patient recovery time, discomfort, and deleterious side effects. Traditional forms of minimally invasive surgery include endoscopy. One of the more common forms of endoscopy is laparoscopy, which is minimally invasive inspection or surgery within the abdominal cavity. In traditional laparoscopic surgery, a patient's abdominal cavity is insufflated with gas, and cannula sleeves are passed through small (approximately 12 mm) incisions in the musculature of the patient's abdomen to provide entry ports through which laparoscopic surgical instruments can be passed in a sealed fashion.

The laparoscopic surgical instruments generally include a laparoscope for viewing the surgical field and surgical instruments having end effectors. Typical surgical tools include clamps, graspers, scissors, staplers, and needle holders, for example. The surgical instruments are similar to those used in conventional (open) surgery, except that the end effector of each surgical instrument is separated from its handle by an approximately 30 cm. long extension tube, for example, so as to permit the operator to introduce the end effector to the surgical site and to control movement of the end effector relative to the surgical site from outside a patient's body.

In order to provide improved control of the working tools, it may be desirable to control the instrument with teleoperated actuators. The surgeon may operate controls on a console to indirectly manipulate the instrument that is connected to the teleoperated actuators. The instrument is detachably coupled to the teleoperated actuators so that the instrument can be separately sterilized and selected for use as needed instrument for the surgical procedure to be performed. The instrument may be changed during the course of a surgery.

Performing surgery with teleoperated surgical instruments creates new challenges. One challenge is the need to maintain the region adjacent the patient in a sterile condition. However, the motors, sensors, encoders and electrical connections that are necessary to control the surgical instruments typically cannot be sterilized using conventional methods, e.g., steam, heat and pressure or chemicals, because they would be damaged or destroyed in the sterilization process.

Another challenge with teleoperated surgery systems is that a surgeon will typically employ a large number of different surgical instruments during a procedure. Since the number of instrument holders are limited due to space constraints and cost, many of these surgical instruments will be attached and detached from the same instrument holder a number of times during an operation. In laparoscopic procedures, for example, the number of entry ports into the patient's abdomen is generally limited during the operation because of space constraints as well as a desire to avoid unnecessary incisions in the patient. Thus, a number of different surgical instruments will typically be introduced through the same trocar sleeve during the operation. Likewise, in open surgery, there is typically not enough room around the surgical site to position more than one or two surgical manipulators, and so the surgeon's assistant will be compelled to frequently remove instruments from the teleoperated actuated manipulator and exchange them with other surgical tools.

It would be desirable to provide an easier and more effective way to engage and disengage a surgical instrument and a teleoperated actuator drive while preventing contamination of the teleoperated actuator and allowing quick and reliable attachment of a succession of surgical instruments that maintains a sterile area around the surgical instrument.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements:

FIG. 6 is an elevation view of a latch plate.

FIG. 7A is a cross-section view of a latch plate.

FIG. 7B is a detail view of an instrument latch arm, a carriage latch arm, and a connecting member from FIG. 7A in a first position.

FIG. 7C is a detail view of an instrument latch arm, a carriage latch arm, and a connecting member from FIG. 7A in a second position.

DESCRIPTION OF EMBODIMENTS

Figure 1:
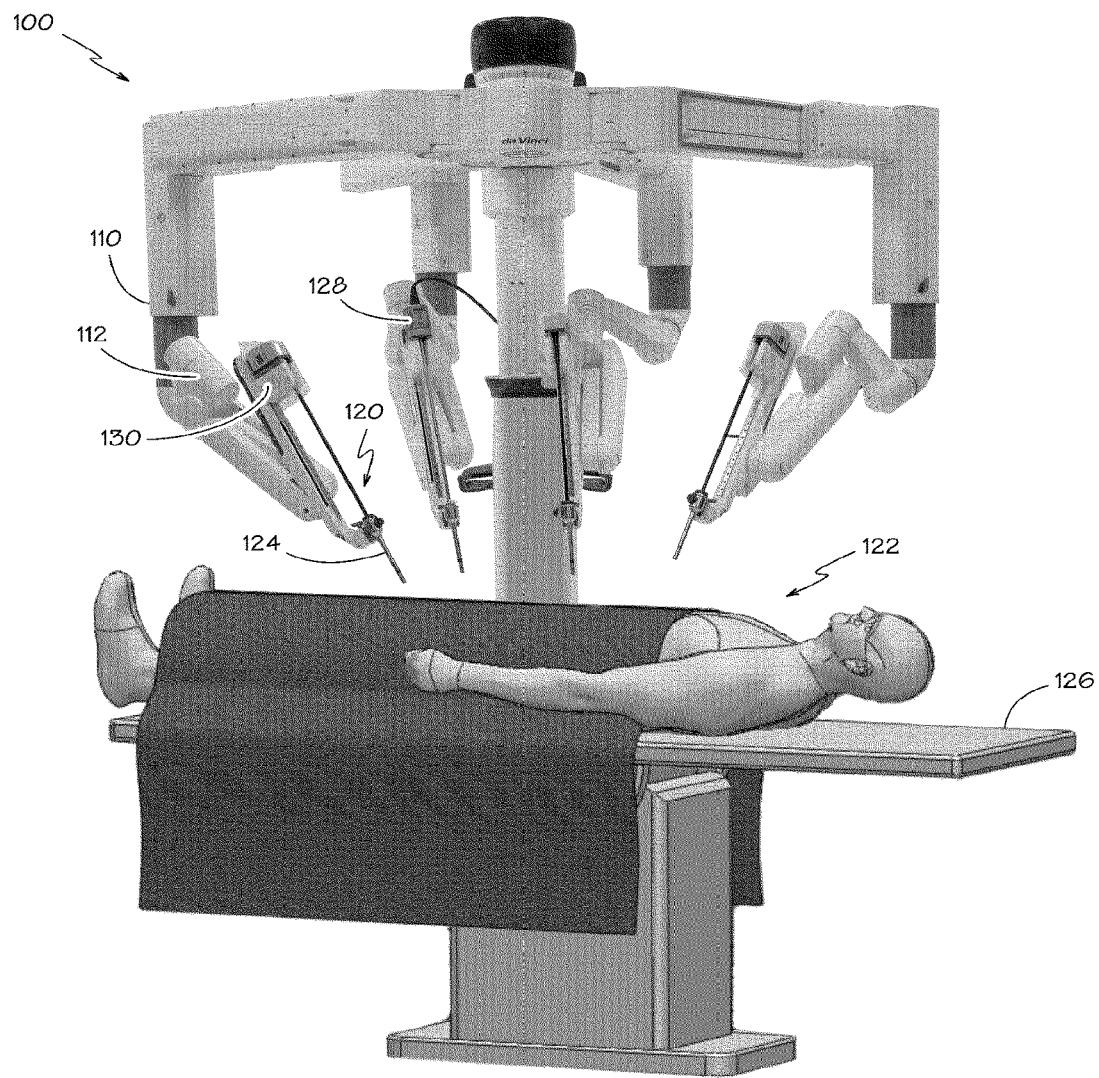
FIG. 1 is a view of an illustrative patient-side portion of a teleoperated surgical system.

In the following description, numerous specific details are set forth. However, it is understood that embodiments of the invention may be practiced without these specific details. In other instances, well-known circuits, structures, and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a," "an," and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The term "object" generally refers to a component or group of components. For example, an object may refer to either a pocket or a boss of a disk within the specification or claims. Throughout the specification and claims, the terms "object," "component," "portion," "part" and "piece" are used interchangeably.

The terms "instrument" and "surgical instrument" are used herein to describe a medical device configured to be inserted into a patient's body and used to carry out surgical or diagnostic procedures. The instrument includes an end effector. The end effector may be a surgical tool associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some instruments used with embodiments of the invention further provide an articulated support (sometimes referred to as a "wrist") for the surgical tool so that the position and orientation of the surgical tool can be manipulated with one or more mechanical degrees of freedom in relation to the instrument's shaft. Further, many surgical end effectors include a functional mechanical degree of freedom, such as jaws that open or close, or a knife that translates along a path. Surgical instruments may also contain stored (e.g., on a semiconductor memory inside the instrument) information that may be permanent or may be updatable by the surgical system. Accordingly, the system may provide for either one-way or two-way information communication between the instrument and one or more system components.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

FIG. 1 is a view of an illustrative patient-side portion 100 of a teleoperated surgical system, in accordance with embodiments of the present invention. The patient-side portion 100 includes support assemblies 110 and one or more instrument carriages 130 that include actuators and control connections for surgical instruments at the end of each support assembly. The support assemblies optionally include one or more unpowered, lockable setup joints that are used to position the instrument manipulator(s) 112 with reference to the patient for surgery. As depicted, the patient-side portion 100 rests on the floor. In other embodiments the patient-side portion may be mounted to a wall, to the ceiling, to the operating table 126, which also supports the patient's body 122, or to other operating room equipment. Further, while the patient-side portion 100 is shown as including four instrument manipulators 112, more or fewer instrument manipulators may be used. Still further, the patient-side portion 100 may consist of a single assembly as shown, or it may include two or more separate assemblies, each optionally mounted in various possible ways.

Each setup joint supports one or more instrument manipulators 112. Each instrument manipulator 112 includes an instrument carriage 130 that supports a surgical instrument 120 for operating at a surgical site within the patient's body 122. Each instrument manipulator 112 may be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each instrument manipulator 112 to move its associated surgical instrument around a center of motion on the surgical instrument that stays stationary with reference to the patient, and this center of motion is typically located to be at the position where the surgical instrument enters the body.

The term "surgical instrument" is used herein to describe a medical device configured to be inserted into a patient's body and used to carry out surgical or diagnostic procedures. The surgical instrument typically includes an end effector associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some surgical instruments used with embodiments of the invention further provide an articulated support (sometimes referred to as a "wrist") for the end effector so that the position and orientation of the end effector can be manipulated with one or more mechanical degrees of freedom in relation to the instrument's shaft. Further, many surgical end effectors include a functional mechanical degree of freedom, such as jaws that open or close, or a knife that translates along a path. Surgical instruments may also contain stored (e.g., on a semiconductor memory inside the instrument) information that may be permanent or may be updatable by the surgical system. Accordingly, the system may provide for either one-way or two-way information communication between the instrument and one or more system components.

A functional teleoperated surgical system will generally include a vision system portion (not shown) that enables the operator to view the surgical site from outside the patient's body 122. The vision system typically includes a surgical instrument that has a video-image-capture function (a camera instrument 128) and one or more video displays for displaying the captured images. In some surgical system configurations, the camera instrument 128 includes optics that transfer the images from the distal end of the camera instrument 128 to one or more imaging sensors (e.g., CCD or CMOS sensors) outside of the patient's body 122. Alternatively, the imaging sensor(s) may be positioned at the distal end of the camera instrument 128, and the signals produced by the sensor(s) may be transmitted along a lead or wirelessly for processing and display on the video display. An illustrative video display is the stereoscopic display on the surgeon's console in surgical systems commercialized by Intuitive Surgical, Inc., Sunnyvale, Calif.

A functional teleoperated surgical system will further include a control system portion (not shown) for controlling the movement of the surgical instruments 120 while the instruments are inside the patient. The control system portion may be at a single location in the surgical system, or it may be distributed at two or more locations in the system (e.g., control system portion components may be in the system's patient-side portion 100, in a dedicated system control console, or in a separate equipment rack). The teleoperated master/slave control may be done in a variety of ways, depending on the degree of control desired, the size of the surgical assembly being controlled, and other factors. In some embodiments, the control system portion includes one or more manually-operated input devices, such as a joystick, exoskeletal glove, a powered and gravity-compensated manipulator, or the like. These input devices control teleoperated motors which, in turn, control the movement of the surgical instrument.

The forces generated by the teleoperated motors are transferred via drivetrain mechanisms, which transmit the forces from the teleoperated motors to the surgical instrument 120. In some telesurgical embodiments, the input devices that control the manipulator(s) may be provided at a location remote from the patient, either inside or outside the room in which the patient is placed. The input signals from the input devices are then transmitted to the control system portion. Persons familiar with telemanipulative, teleoperative, and telepresence surgery will know of such systems and their components, such as the da Vinci® Surgical System commercialized by Intuitive Surgical, Inc. and the Zeus® Surgical System originally manufactured by Computer Motion, Inc., and various illustrative components of such systems.

As shown, both the surgical instrument 120 and an optional entry guide 124 (e.g., a cannula in the patient's abdomen) are removably coupled to the distal end of an instrument manipulator 112, with the surgical instrument 120 inserted through the entry guide 124. Teleoperated actuators in the instrument manipulator 112 move the surgical instrument 120 as a whole. The instrument manipulator 112 further includes an instrument carriage 130. The surgical instrument 120 is detachably connected to the instrument carriage 130. The teleoperated actuators housed in the instrument carriage 130 provide a number of controller motions which the surgical instrument 120 translates into a variety of movements of the end effector on the surgical instrument. Thus the teleoperated actuators in the instrument carriage 130 move only one or more components of the surgical instrument 120 rather than the instrument as a whole. Inputs to control either the instrument as a whole or the instrument's components are such that the input provided by a surgeon to the control system portion (a "master" command) is translated into a corresponding action by the surgical instrument (a "slave" response).

Figure 2:
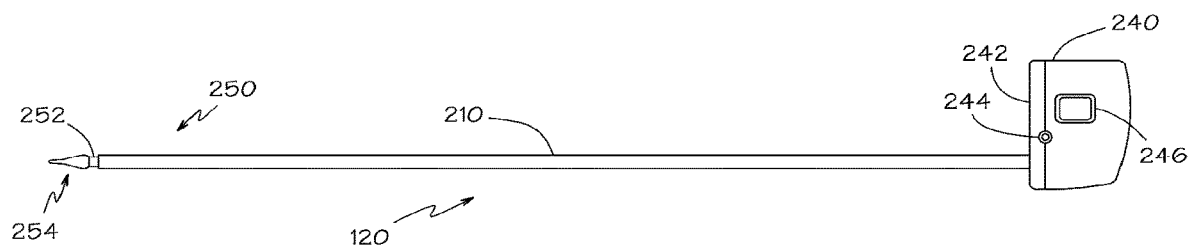
FIG. 2 is a side view of a surgical instrument for use with a teleoperated actuator.

FIG. 2 is a side view of an illustrative embodiment of the surgical instrument 120, comprising a distal portion 250 and a proximal control mechanism 240 coupled by an elongate tube 210. The proximal control mechanism 240 includes an instrument control surface 242 that provides connections to the control features of the surgical instrument 120. The instrument control surface 242 is latched to the instrument carriage 130, which controls the surgical instrument 120.

The distal portion 250 of the surgical instrument 120 may provide any of a variety of surgical tools, such as the forceps 254 shown, a needle driver, a cautery device, a cutting tool, an imaging device (e.g., an endoscope or ultrasound probe), or a combined device that includes a combination of two or more various tools and imaging devices. In the embodiment shown, the forceps 254 are coupled to the elongate tube 210 by a "wrist joint" 252 that allows the orientation of the forceps to be manipulated with reference to the elongate tube 210.

Surgical instruments that are used with the invention may control their end effectors (surgical tools) with a plurality of rods and/or flexible cables. Rods, which may be in the form of tubes, may be combined with cables to provide a "push/pull" control of the end effector with the cables providing flexible sections as required. A typical elongate tube 210 for a surgical instrument 120 is small, perhaps five to eight millimeters in diameter, roughly the diameter of a large soda straw. The diminutive scale of the mechanisms in the surgical instrument 120 creates unique mechanical conditions and issues with the construction of these mechanisms that are unlike those found in similar mechanisms constructed at a larger scale, because forces and strengths of materials do not scale at the same rate as the size of the mechanisms. The cables must fit within the elongate tube 210 and be able to bend as they pass through the wrist joint 252.

In order to provide a sterile operation area while using a functional teleoperated surgical system, it is preferred that a barrier be placed between the actuating portion of the teleoperated surgical system and the surgical instruments in the sterile surgical field. Therefore, a sterile component, such as an instrument sterile adapter (ISA), is placed between the surgical instrument 120 and the teleoperated controls in the instrument carriage 130. The placement of an instrument sterile adapter between the surgical instrument 120 and the instrument carriage 130 includes the benefit of ensuring a sterile coupling point for the surgical instrument 120 and the instrument carriage 130. This permits removal of surgical instruments from the instrument carriage 130 and exchange with other surgical instruments during the course of a surgery.

Figure 3A:
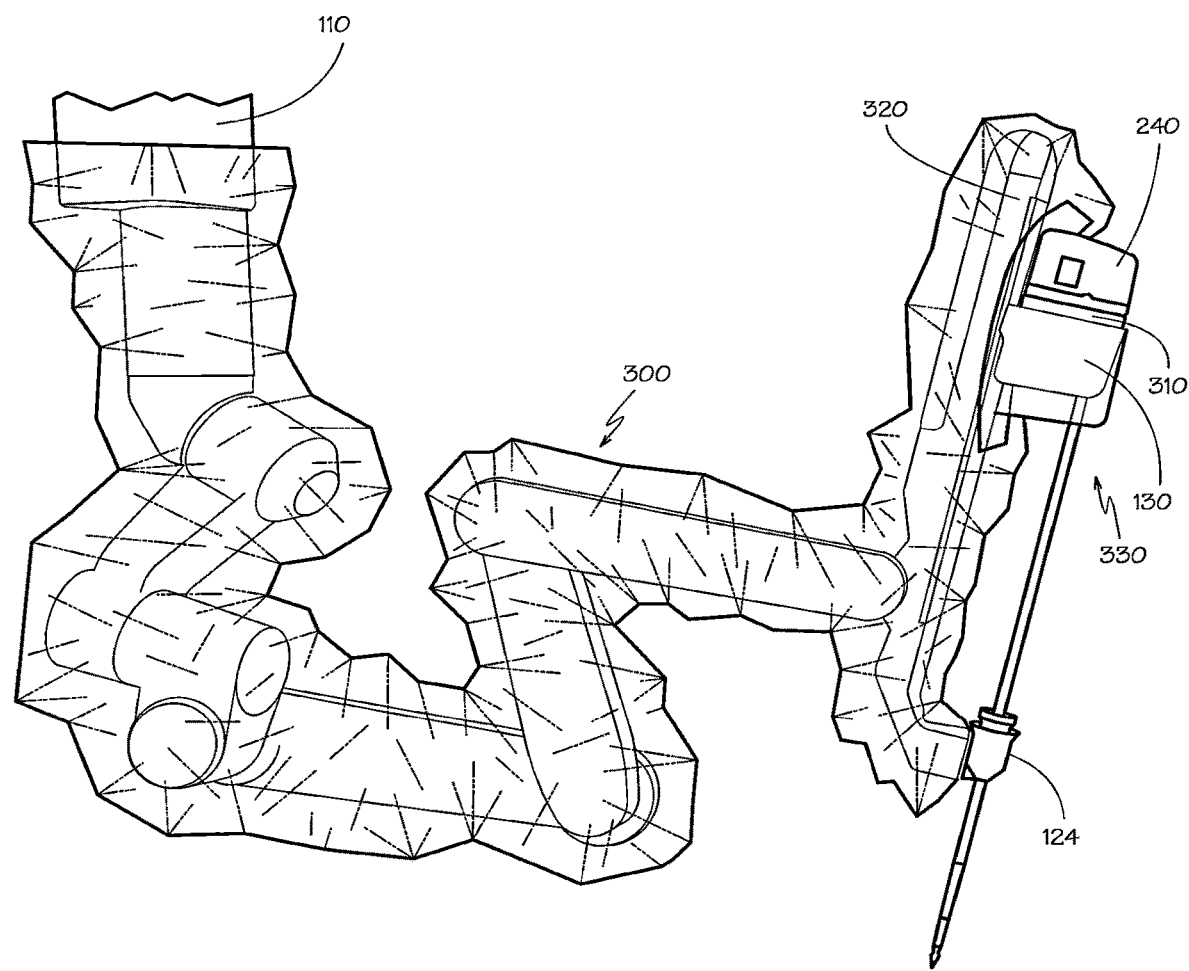
FIG. 3A is a perspective view of a setup joint with a sterile drape.

FIG. 3A is a perspective view of a setup joint that supports the instrument carriage 130 which in turn supports the surgical instrument 120 on a strut 320. In preparation for surgery, the setup joint is covered with a sterile drape 300. The sterile drape protects the setup joint from contamination and provides a sterile surface around the setup joint. The majority of the sterile drape 300 is a plastic sheet, which may be in the form of a tube or bag, that covers the arms of the setup joint. For example, a single layer thermoplastic polyurethane (TPU) may be used. A lubricant may be included to reduce the tackiness of the plastic. The sheet may be about 0.004" thick. Other suitable materials may be used for the sheet. The sterile drape 300 includes a pouch portion 330 that is formed to fit around the instrument carriage 130.

Figure 3B:
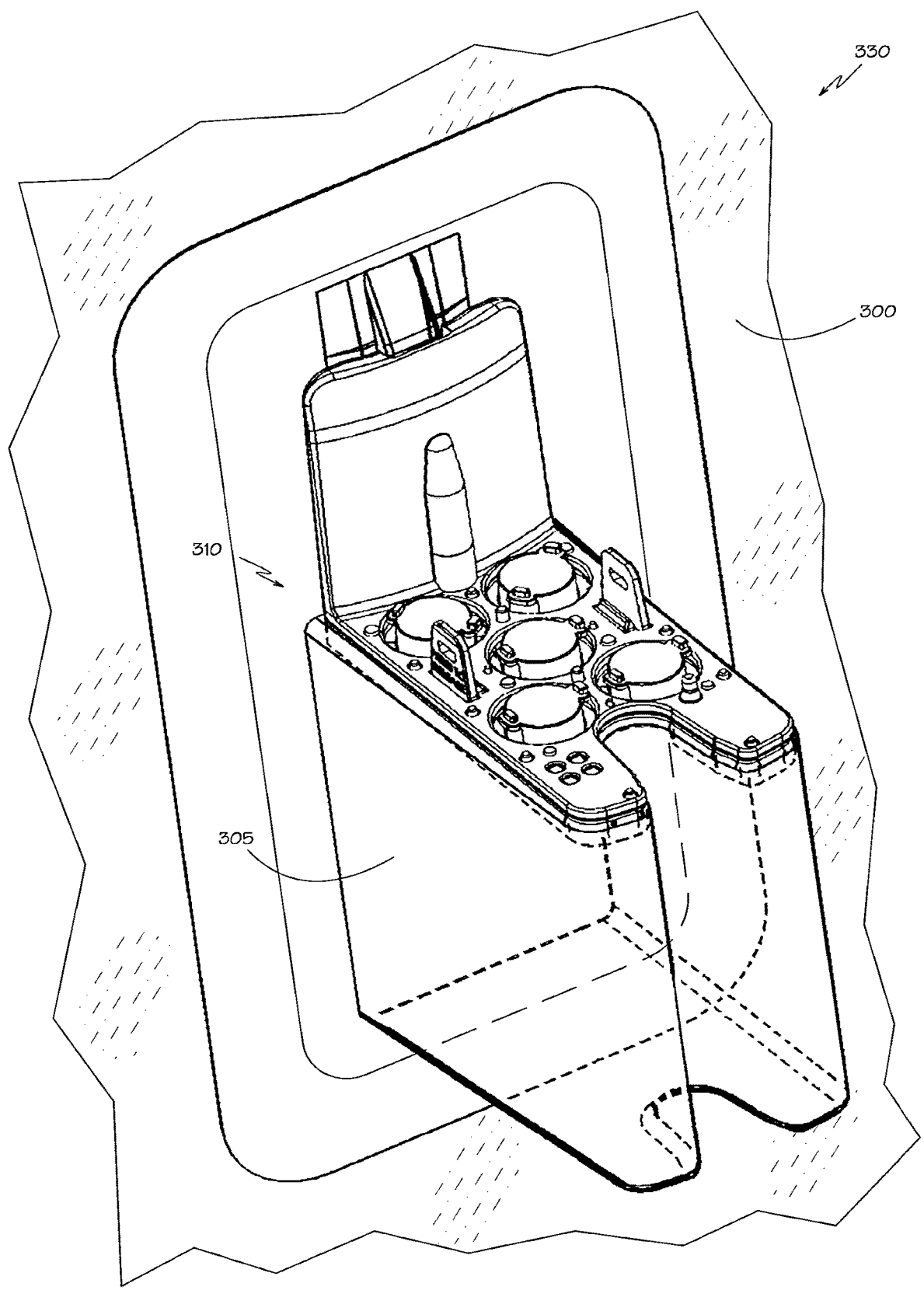
FIG. 3B is a close up view of a portion of the sterile drape shown in FIG. 3A.

FIG. 3B is a perspective view of the pouch portion 330 of the sterile drape 300 shown in FIG. 3A. The pouch portion 330 includes a sterile cover 305 and an instrument sterile adapter 310. The instrument carriage may contain motors, electrical power, and control signals used by a control system to drive the surgical instrument. The instrument sterile adapter 310 transfers motion and electrical signals between the instrument carriage 130 and an instrument control surface 242 of a proximal control mechanism 240 of a surgical instrument 120 connected to the sterile side of the instrument sterile adapter 310. The instrument sterile adapter 310 includes a latch plate provided to secure the connections between instrument sterile adapter 310 and instrument carriage 130 and between instrument sterile adapter 310 and surgical instrument 120.

Figure 4A:
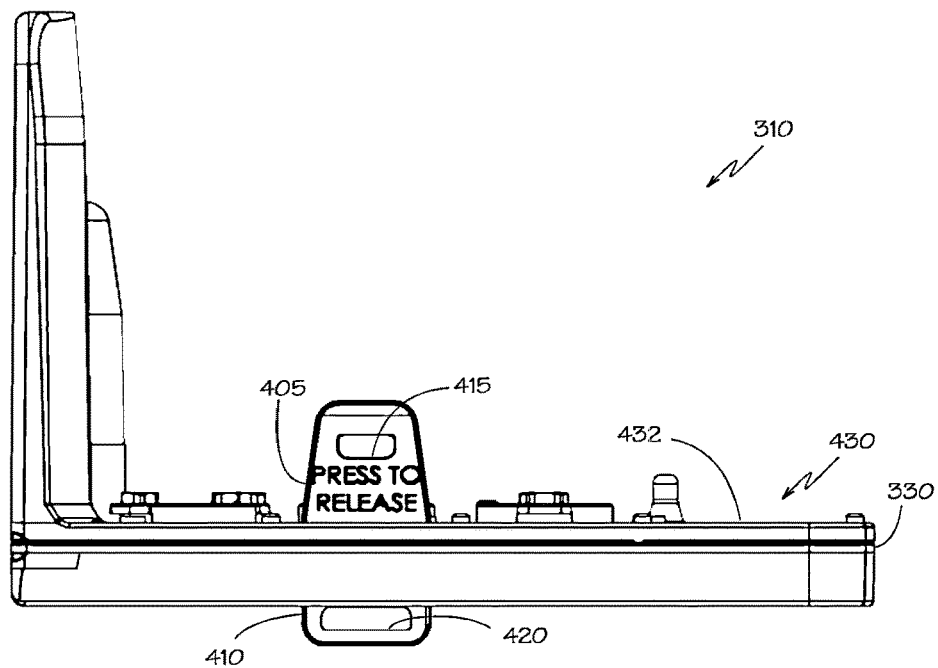
FIG. 4A is a side elevation of the instrument sterile adapter from the sterile drape.
Figure 4B:
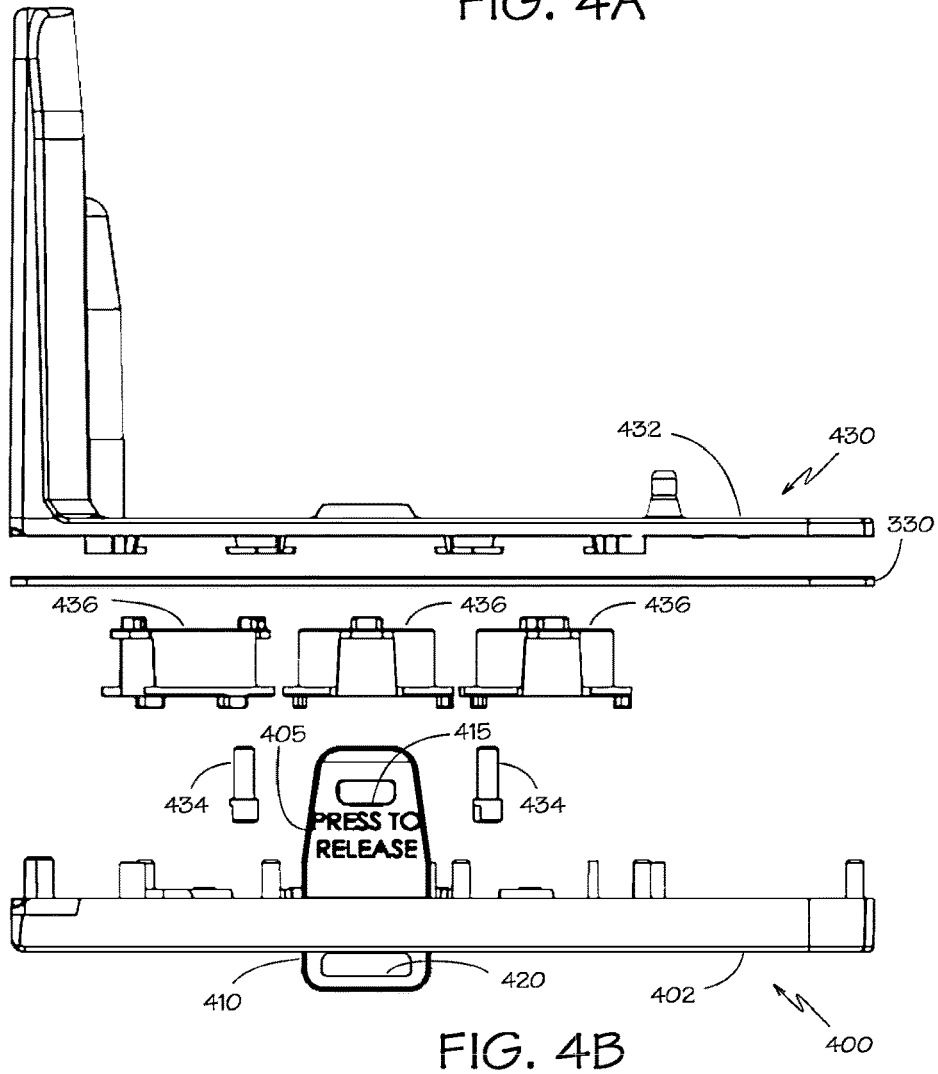
FIG. 4B is an exploded view of the instrument sterile adapter.
Figure 5A:
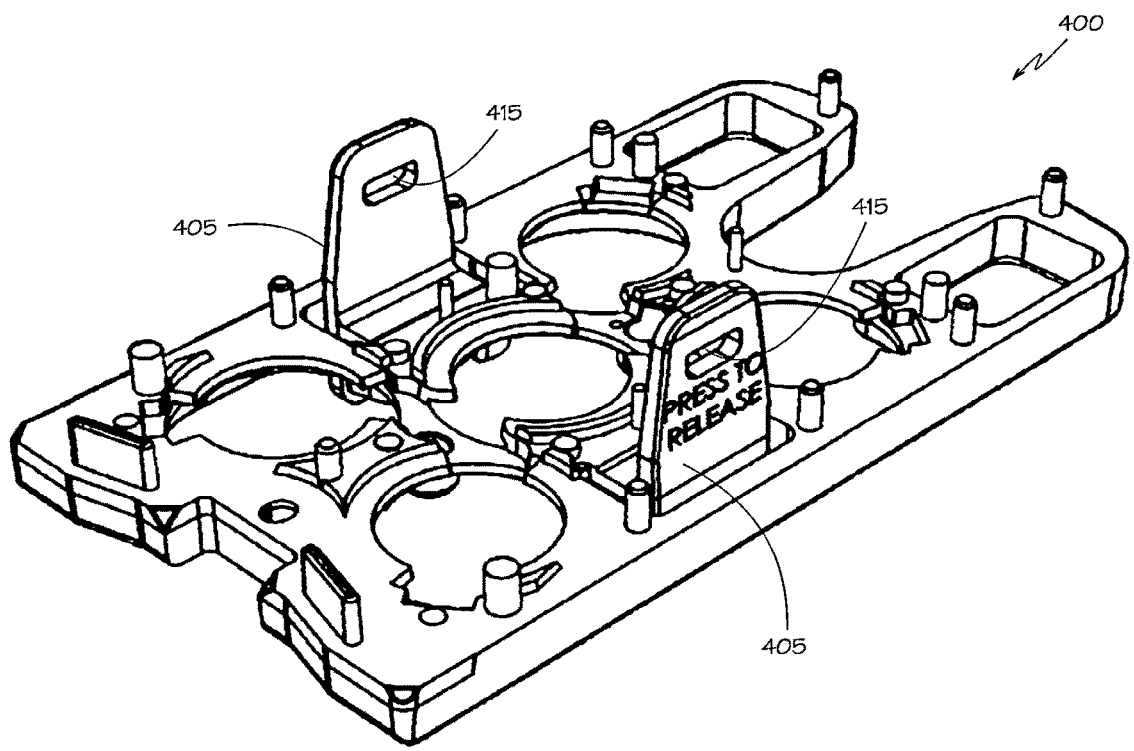
FIG. 5A is a top perspective view of a latch plate.
Figure 5B:
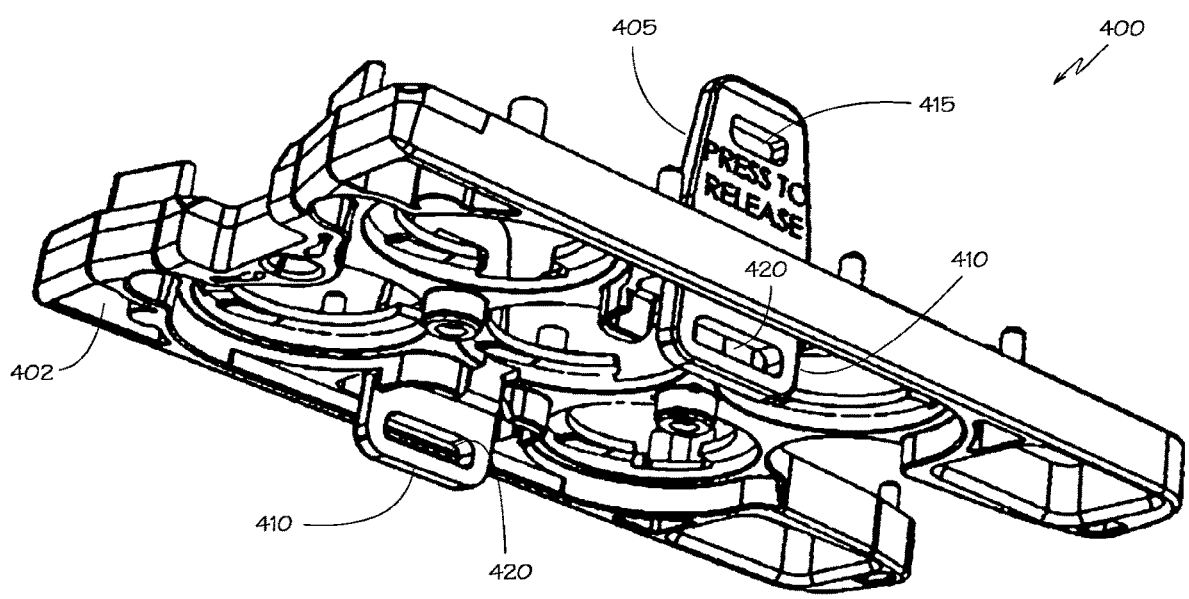
FIG. 5B is a bottom perspective view of a latch plate.

FIG. 4A is a side elevation of the instrument sterile adapter 310 from the sterile drape. FIG. 4B is an exploded view of the instrument sterile adapter. The instrument sterile adapter includes a latch plate 400 and an instrument plate 430 that are joined together to capture a portion of the pouch 330 between the two plates. The latch plate 400 provides a surface 402 to be joined to the instrument carriage 130. The instrument plate 430 provides a surface 432 to receive a surgical instrument 120. Other components used to transfer control motion and signals between a surgical instrument 120 and the instrument carriage 130, such a coupler disks 436 and presence pins 434, may also be captured between the latch plate 400 and the instrument plate 430. The latch plate 400 further provides latches that hold the instrument sterile adapter 310 on the instrument carriage 130 and hold the surgical instrument 120 on the instrument sterile adapter.

Referring to FIGS. 5A, 5B, 6, 7A, 7B, and 7C, a top perspective view, a bottom perspective view, an elevation view, and cross-section views of a latch plate 400 according to one embodiment of the invention are illustrated, respectively. The latch plate 400 includes a pair of instrument latch arms 405 on a first side of the latch plate, and includes a pair of carriage latch arms 410 on a second side. The instrument latch arms 405 are longer than the carriage latch arms 410. A penetrating opening or aperture is provided toward the end portion of each of the latch arms 405, 410, acting as latch receivers. Therefore, each of the instrument latch arms 405 includes an instrument latch receiver 415, and each of the carriage latch arms 410 includes a carriage latch receiver 420. The instrument latch arms 405 are used to secure a surgical instrument 120 to the instrument sterile adapter 310, and the carriage latch arms 410 are used to secure the instrument sterile adapter 310 to an instrument carriage.

FIG. 7A is a cross-section view of latch plate 400 through the plane indicated by section line 7-7 in FIG. 6. As can be seen in FIG. 7A, the instrument latch arms 405, the carriage latch arms 410, and connecting members 425 may be formed in one piece with the latch plate 400, and may be made of a flexible material that returns to its original shape when no external force is applied, such as a plastic material.

FIGS. 7B and 7C show cross-section views of a single latch arm structure in isolation through the plane indicated by section line 7-7 in FIG. 6. An instrument latch arm 405, a corresponding carriage latch arm 410, and a corresponding connecting member 425 form a "T" shape, with the latch arms 405, 410 being the two arms of the letter T, and the connecting member 425 being the stem of the letter T. The instrument latch arm extends through the instrument plate 430 and away from the surface 432 of the instrument plate that receives the surgical instrument. The carriage latch arm 410 extends away from the surface 402 of the latch plate 400 that receives the instrument carriage 130. The instrument latch arm 405 is joined to the carriage latch arm 410 at a junction. The connecting member 425 is joined to both arms at the junction. The connecting member 425 is perpendicular to the carriage latch arm and the instrument latch arm when in its undeformed configuration. As suggested by FIG. 7C, portions of the latch arm structure may be elastically deformed for latching and unlatching. The connecting member 425 provides a flexible connection of the carriage latch arm 410 and the instrument latch arm 405 to a remainder of the latch plate 400. Skilled artisan may appreciate that features may be provided to prevent any of elements discussed above from being deformed past its elastic range.

FIG. 7B shows the latch arms 405, 410 and the connecting member 425 in their original state. FIG. 7C shows the latch arms 405, 410 and the connecting member 425 in a bent state where the instrument latch arm 405 has moved away from the center line of the latch plate 400, the carriage latch arm 410 has moved toward the center line of the latch plate, and the connecting member 425 has moved upwardly toward the carriage latch arm.

As can be seen in FIG. 7C, the latch arms 405, 410 may be slightly and pivotally bent inward or outward approximately around the corresponding connecting member 425 when forces are applied to the latch arms, and of course, the corresponding connecting member 425 may be slightly deformed accordingly. In other words, when an inward or outward force is applied to a latch arm 405, 410, a Class 1 lever is formed with the corresponding connecting member 425 being approximately the fulcrum. (A Class 1 lever is a lever in which the fulcrum is situated between the effort and the resistance.) Absent interference from other objects, bending an instrument latch arm 405 inward causes the corresponding carriage latch arm 410 to move outward, and vice versa. Bending a carriage latch arm 410 has the same effects on the corresponding instrument latch arm 405.

FIGS. 8A, 8B, 8C, and 8D are cross-section views of the instrument sterile adapter 310 including a latch plate 400 through the plane indicated by section line 7-7 in FIG. 6. FIGS. 8A, 8B, 8C, and 8D show the assembly sequence of the instrument sterile adapter 310 to a control surface 805 of an instrument carriage 130 and a proximal control mechanism 240 of a surgical instrument 120 to the instrument sterile adapter.

Figure 8A:
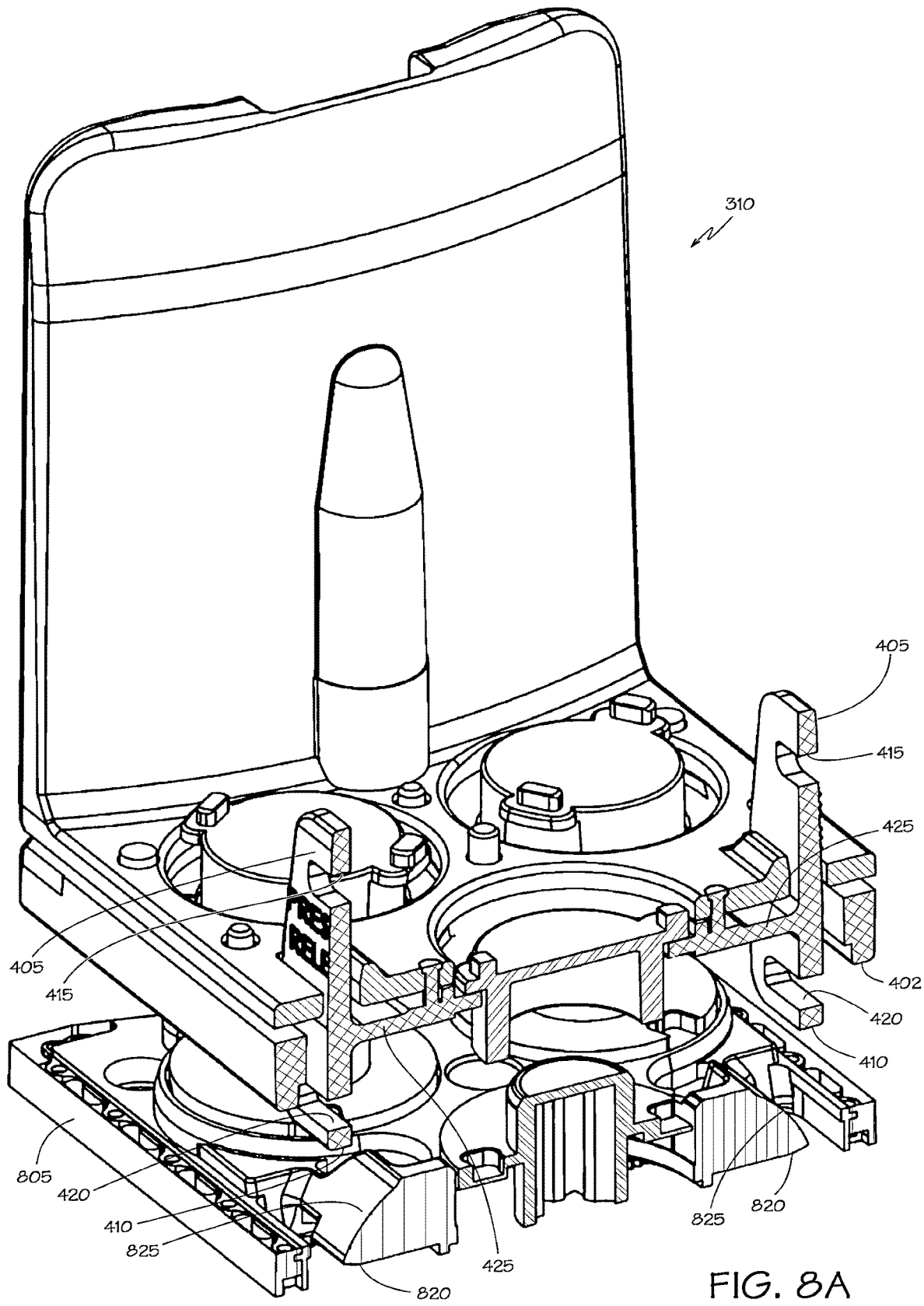
FIG. 8A is a cross-section view of an adapter separated from an instrument carriage.

Referring to FIG. 8A, the control surface 805 of the instrument carriage includes a first fixed latch structure that provides two first angled lead-in latch surfaces 825 leading to two first locking surfaces 820. The first fixed latch structure may be made of a rigid material that does not deform easily. The two first angled lead-in latch surfaces 825 help guide the carriage latch arms 410 into the first fixed carriage latch structure when one attempts to attach the instrument sterile adapter 310 to the control surface 805. The instrument sterile adapter 310 typically includes a translucent pouch that surrounds the instrument carriage 130 when the instrument sterile adapter 310 is attached to the control surface 805. The pouch may largely obstruct the view of the carriage latch structure as the instrument sterile adapter 310 is being attached to the control surface 805. The two first angled lead-in latch surfaces 825 may provide a "saddle-like" receiving surface for the carriage latch arms 410 facilitating the attachment of the instrument sterile adapter 310 to the control surface 805 by feel. When the instrument sterile adapter 310 is being attached to the control surface 805, the angled lead-in latch surfaces 825 will cause the latch arm structures to elastically deform to allow the carriage latch arms 410 to pass over the angled lead-in latch surfaces.

Figure 8B:
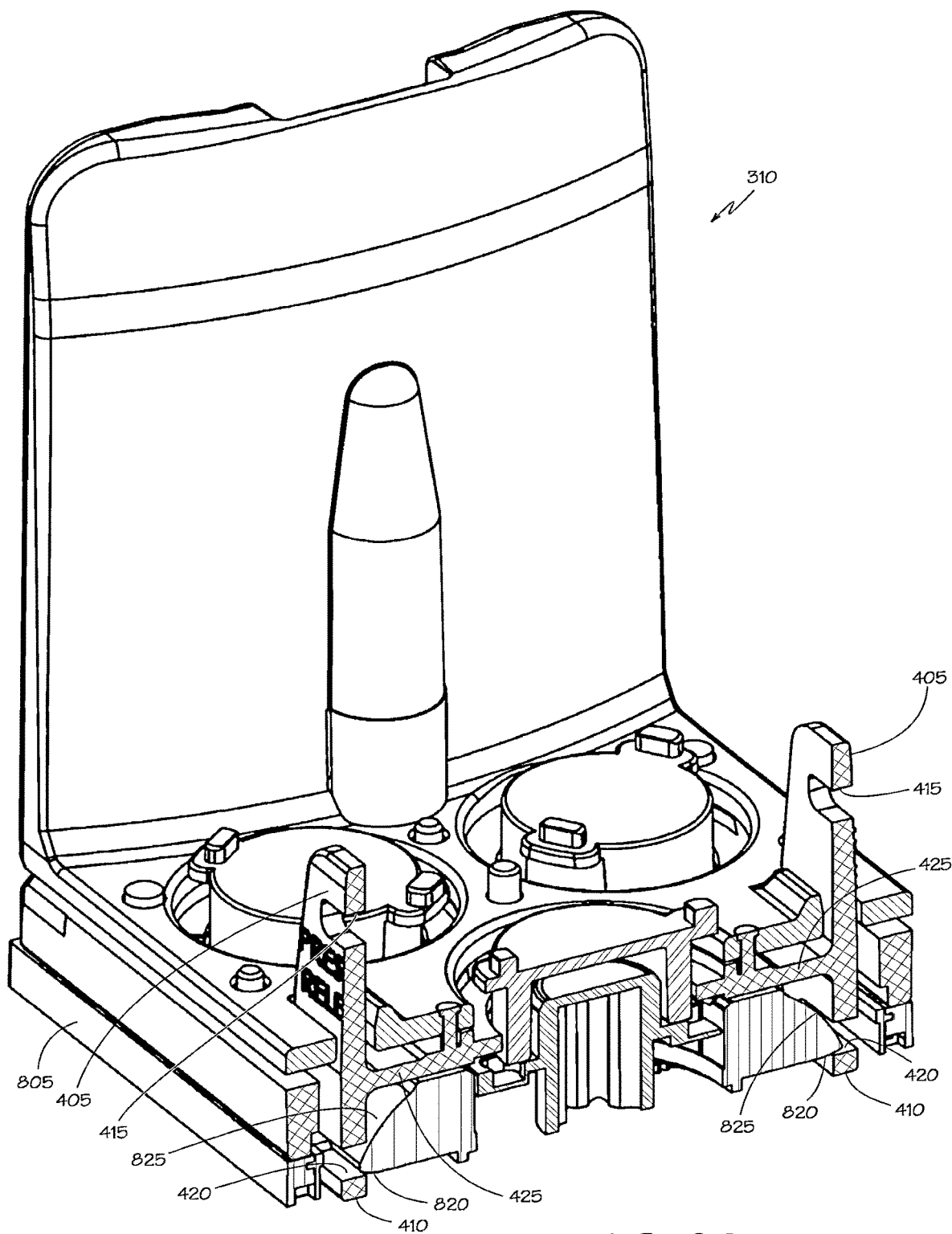
FIG. 8B is a cross-section view of the adapter latched to the instrument carriage.

Referring to FIG. 8B, when the instrument sterile adapter 310 is attached to the control surface 805, the first locking surfaces 820 of the control surface 805 engage the carriage latch receivers 420 of the carriage latch arms 410 of the latch plate 400. The elastic deformation of the latch arm structures is largely released when the carriage latch receivers 420 engage the first locking surfaces 820. This secures the instrument sterile adapter 310 to the control surface 805. The carriage latch structure of the control surface 805 supports the carriage latch arms 410 and prevents them from rotating inwardly toward each other. This in turn prevents the connecting members 425 from bending from their undeformed configuration.

Figure 8C:
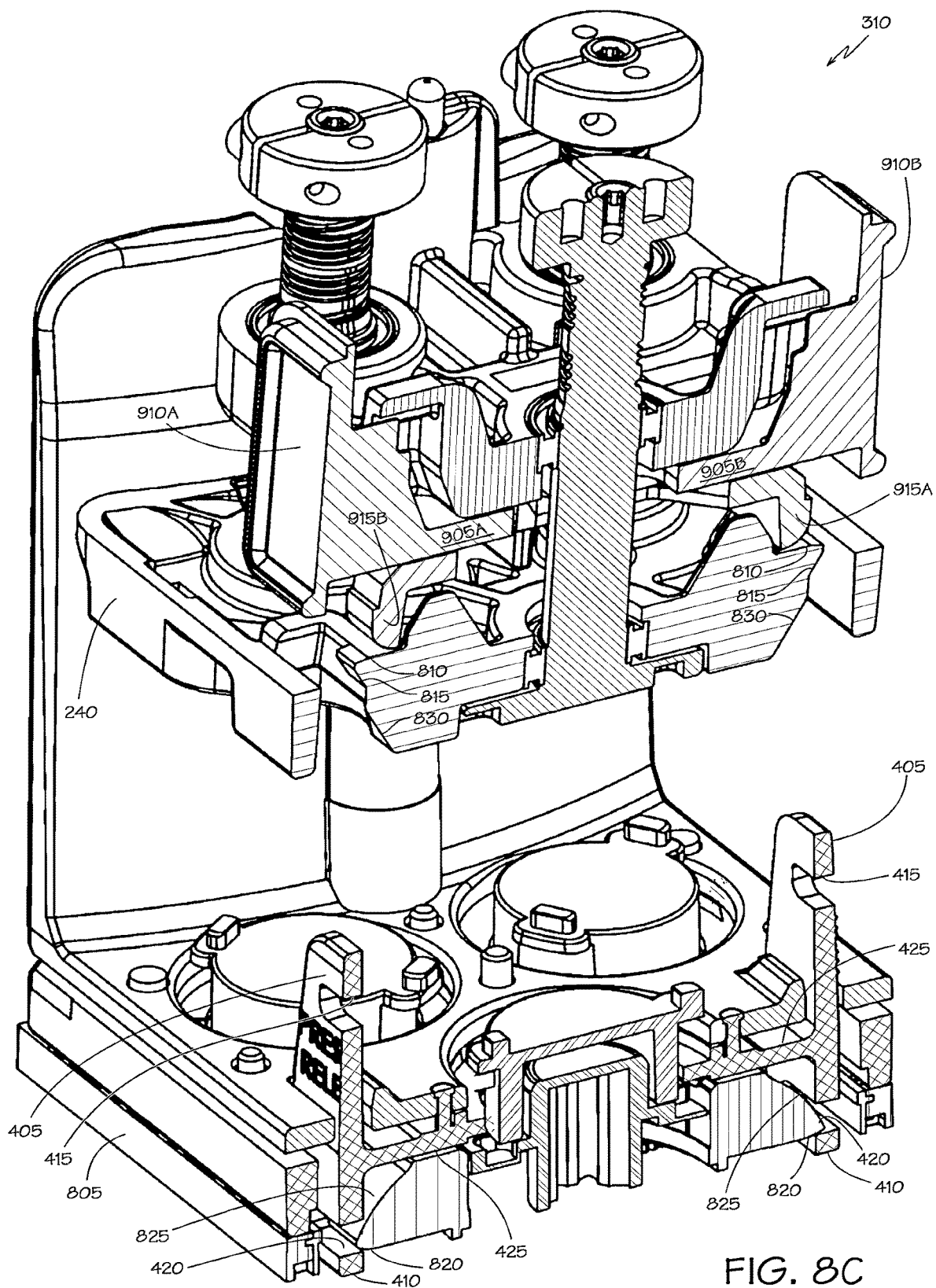
FIG. 8C is a cross-section view of a proximal control mechanism separated from the adapter and instrument carriage.

Referring to FIG. 8C, the proximal control mechanism 240 includes a second fixed latch structure that provides two second angled lead-in latch surfaces 815 leading to two second locking surfaces 810. The lead-in ramps 830 may be formed as part of the instrument latch structure. The second fixed latch structure may be made of a rigid material that does not deform easily. The second fixed instrument latch structure of the proximal control mechanism 240 further includes two lead-in ramps 830 that help guide the instrument latch arms 405 of the instrument sterile adapter 310 into the instrument latch structure when one attempts to attach the proximal control mechanism 240 to the instrument sterile adapter 310. The help afforded by the lead-in ramps 830 is desirable because direct view of relevant components is partially or fully obstructed by the proximal control mechanism 240, which is enclosed by a housing not shown in FIG. 8C but which can be seen in FIG. 2.

Figure 8D:
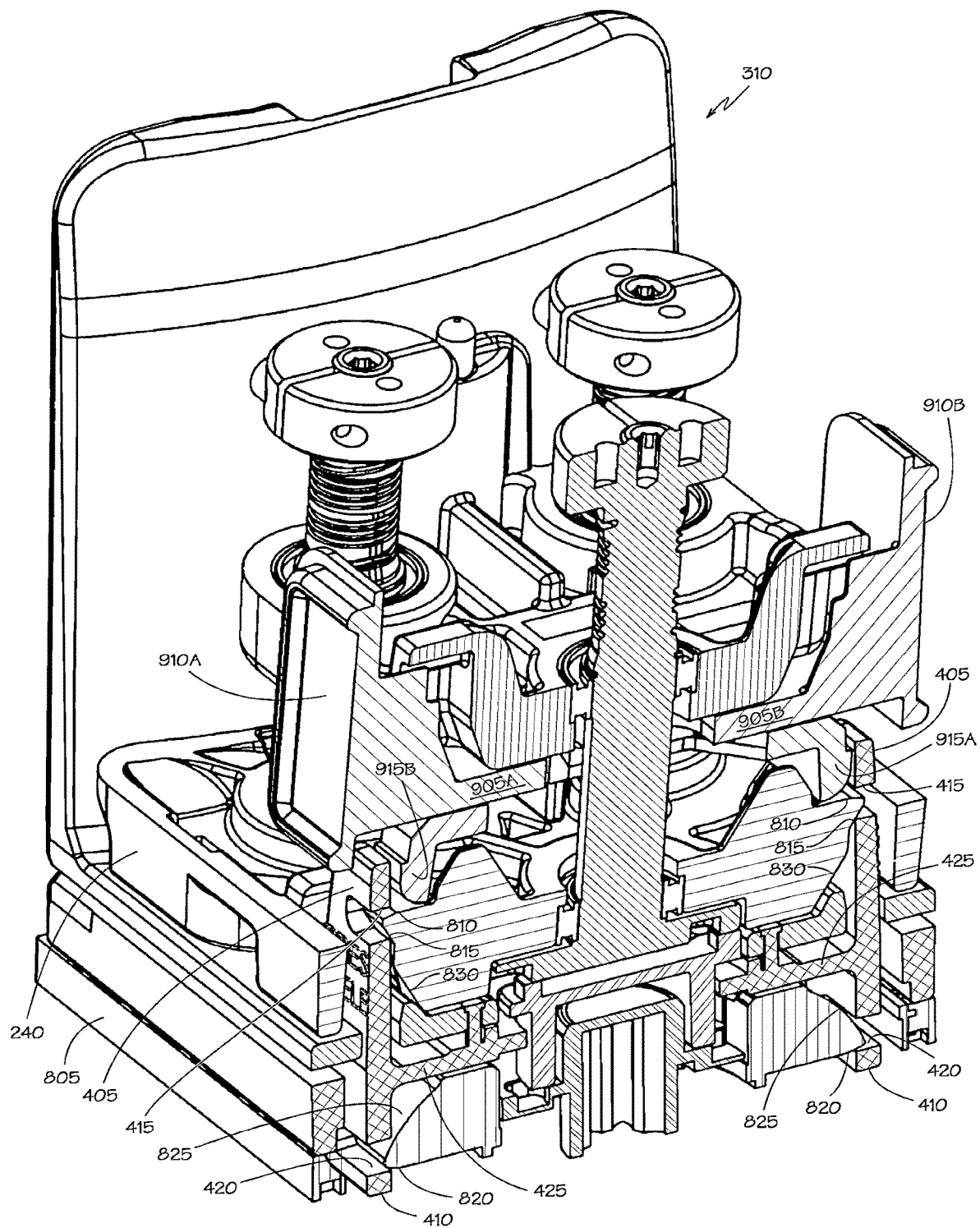
FIG. 8D is a cross-section view of the proximal control mechanism latched to the adapter and instrument carriage.

Referring to FIG. 8D, when the proximal control mechanism 240 of the surgical instrument 120 is attached to the instrument sterile adapter 310, the second locking surfaces 810 of the proximal control mechanism 240 engage the instrument latch receivers 415 of the instrument latch arms 405 of the latch plate 400. This secures the proximal control mechanism 240 of the surgical instrument 120 to the instrument sterile adapter 310. It will be appreciated that the instrument latch arms 405 must be sufficiently flexible to bend outwardly to pass over the second angled lead-in latch surfaces 815 because the connecting members 425 are prevented from bending toward the instrument carriage 130 by the carriage latch arms 410 when the instrument sterile adapter 310 is attached to the control surface 805.

It should be appreciated that when both the proximal control mechanism 240 of the surgical instrument 120 and the control surface 805 of the instrument carriage are attached to the instrument sterile adapter 310, the presence of the proximal control mechanism 240 constitutes a locking mechanism for the attachment of the instrument sterile adapter 310 to the instrument carriage 130. Inward movement of the instrument latch arms 405 is prevented by the attached proximal control mechanism 240. In turn, upward movement of the connecting members 425 away from the control surface is prevented by the constrained instrument latch arms 405. As a result, outward movement of carriage latch arms 410 becomes difficult. The carriage latch arms 410 may be short and of a greater thickness to further increase the difficulty of disengaging the carriage latch arms when the proximal control mechanism 240 is attached to the instrument sterile adapter 310. Because carriage latch arms 410 are prevented from being bent outward by the proximal control mechanism 240, the instrument sterile adapter 310 is locked to the attached control surface 805.

FIGS. 9A through 9H show cross-section views of a single latch arm structure with the fixed latch structures of a control surface 805 of an instrument carriage 130 and a proximal control mechanism 240 through the plane indicated by section line 7-7 in FIG. 6.

Figure 9A:
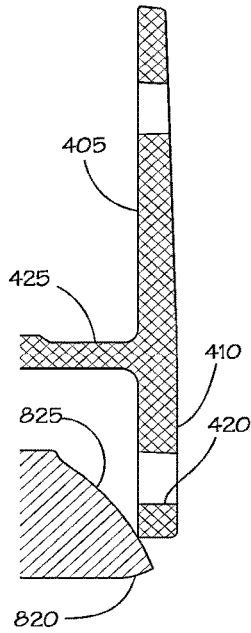
FIGS. 9A through 9H are cross-sectional views of a proximal control mechanism, an adapter, and an instrument carriage in various stages of the latching process.

Referring to FIG. 9A, the instrument sterile adapter is being attached to the instrument carriage. To attach the instrument sterile adapter 310 to the control surface 805 of an instrument carriage 130, one roughly aligns the instrument sterile adapter with the control surface, and pushes the instrument sterile adapter against the control surface. The first angled lead-in latch surface 825 can help guide the carriage latch arms 410 into the carriage latch structure and provide the necessary rough alignment. The latch arm structure of the instrument sterile adapter is shown at the point where elastic deformation of the latch arm structure is about to begin.

Figure 9B:
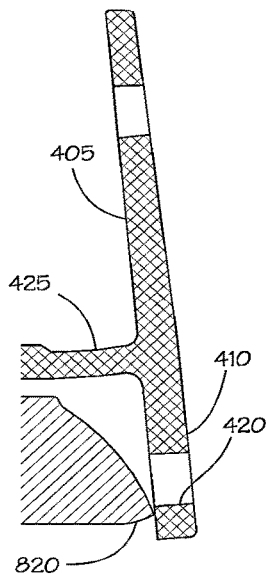

Referring to FIG. 9B, as the instrument sterile adapter is pressed toward the control surface, the latch arm structure of the instrument sterile adapter deforms to allow the carriage latch arm 410 to pass over the locking surface 820. The connecting member 425 may be sized and shaped so that most of the elastic deformation occurs in the connecting member when the carriage latch arm 410 passes over the locking surface 820. The connecting member 425 may be sufficiently flexible to cause the carriage latch arm 410 to rotate and allow the carriage latch arm to pass over the fixed locking surface 820 in the instrument carriage. As the instrument sterile adapter is being pushed against the control surface, the first angled latch surface 825 pushes the carriage latch arm 410 outward, allowing the instrument sterile adapter 310 to move toward the control surface.

Figure 9C:
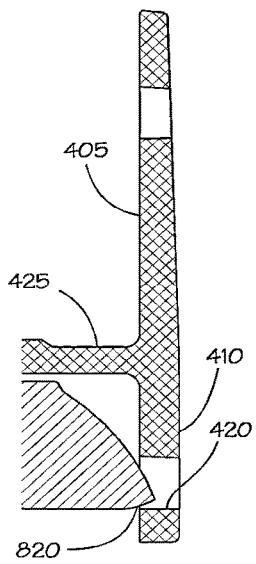

Referring to FIG. 9C, the instrument sterile adapter is moved toward the control surface until the first locking surface 820 enters the carriage latch receiver 420, at which time and the connecting member 425 may resume an original shape and cause the carriage latch arm 410 to engage the first fixed locking surface. The carriage latch arms 410 close in on the carriage latch structure, securing the instrument sterile adapter to the control surface of an instrument carriage 130. In this condition the instrument sterile adapter is ready to receive a proximal control mechanism of a surgical instrument. In some embodiments, the pair of carriage latch arms 410 may be shaped and/or spaced such that when the pair of carriage latch arms 410 are closed on the carriage latch structure, the pair of carriage latch arms 410 are bent slightly outward compared to their natural shape so that they apply inward forces on the carriage latch structure to better secure the instrument sterile adapter to the instrument carriage.

Figure 9D:
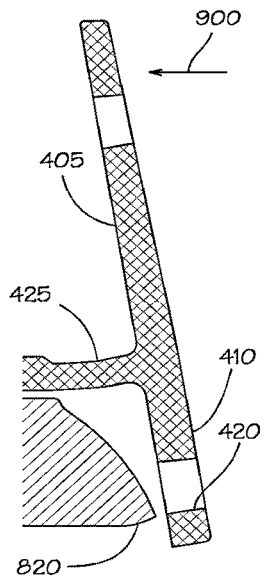

Referring to FIG. 9D, the instrument latch arm 405 may be used as a release lever for the carriage latch arms 410. The instrument latch arm 405 can receive a force 900 that bends the connecting member 425 sufficiently to cause the carriage latch arm 410 to rotate and allow the carriage latch arm pass over a fixed locking surface in the instrument carriage. By pressing the two instrument latch arms 405 toward the center of the latch plate 400 with a force 900 as indicated by the arrow, for example by pinching the two instrument latch arms, the carriage latch arms 410 are moved outwardly. This releases the carriage latch receiver 420 from the first locking surface 820 of the carriage latch structure and allows the instrument sterile adapter to be removed from the instrument carriage.

Figure 9E:
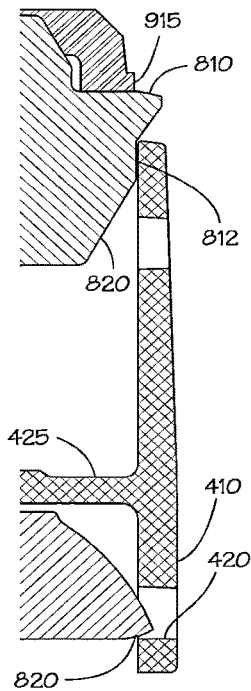

Referring to FIG. 9E, a proximal control mechanism of a surgical instrument is being attached to the instrument sterile adapter. The instrument sterile adapter is in the condition shown in FIG. C. To attach the proximal control mechanism of a surgical instrument to the instrument sterile adapter, one roughly aligns the proximal control mechanism with the instrument sterile adapter, and pushes the proximal control mechanism toward the instrument sterile adapter. The lead-in ramp 830 helps guide the instrument latch arm 405 into the fixed instrument latch structure and provides the necessary rough alignment. A transition section 812 may join the lead-in ramp 830 to the second locking surface 810. The transition section 812 may be generally parallel to the undeformed instrument latch arm 405. The transition section 812 may be located to closely fit against the instrument latch arm 405 when the proximal control mechanism is positioned to be latched to the instrument sterile adapter. The transition section 812 may hold the surgical instrument in place to allow for preparation of the instrument prior to latching to the instrument sterile adapter. The latch arm structure of the instrument sterile adapter is shown at the point where elastic deformation of the latch arm structure is about to begin.

Figure 9F:
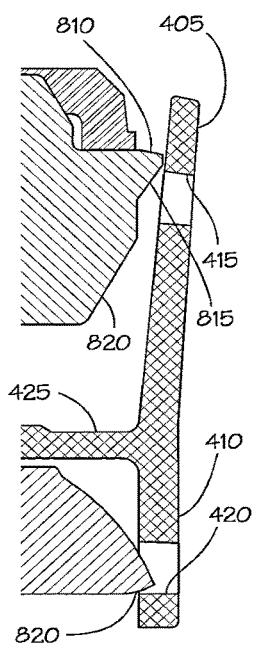

Referring to FIG. 9F, the proximal control mechanism is being attached to the instrument sterile adapter. As the proximal control mechanism is pushed toward the instrument sterile adapter, the second angled latch surface 815 pushes on the instrument latch arm 405 and bends it away from the fixed instrument latch structure. The instrument latch arm 405 is sufficiently flexible to pass over the fixed locking surface in the surgical instrument. This allows the instrument latch arm 405 to pass over the second locking surface 810.

Figure 9G:
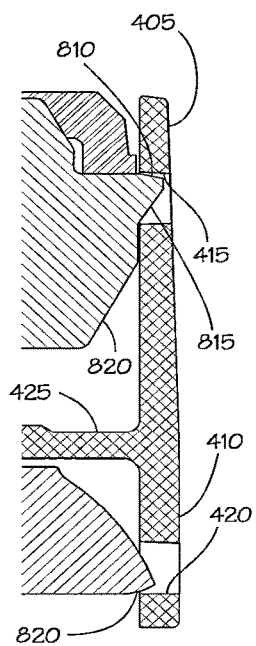

Referring to FIG. 9G, the proximal control mechanism is moved toward the instrument sterile adapter until the second locking surface 810 enters the instrument latch receiver 415 and the instrument latch arm resumes an original undeformed shape to engage the second fixed locking surface. The instrument latch arm 405 closes in on the fixed instrument latch structure of the proximal control mechanism, securing the proximal control mechanism to the instrument sterile adapter. In some embodiments, the instrument latch arms 405 may be shaped and/or spaced such that when the instrument latch arms 405 are closed on the fixed instrument latch structure, the instrument latch arms are bent slightly outward compared to their natural undeformed shape so that they apply inward forces on the fixed instrument latch structure to better secure the proximal control mechanism to the instrument sterile adapter. Securing the proximal control mechanism to the instrument sterile adapter may prevent the carriage latch arm 410 and the connecting member 425 from moving away from the first locking surface 820, thus providing an interlock of the attachment of the instrument sterile adapter to the instrument carriage.

Figure 9H:
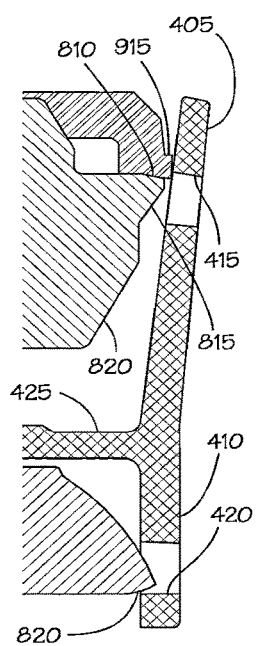

Referring to FIG. 9H, a latch release that includes a latch arm engaging portion 915 may be used to release the instrument latch arm 405 from the second locking surface 810. It will be appreciated that when the instrument sterile adapter is coupled to the instrument carriage and the proximal control mechanism is coupled to the instrument sterile adapter, the entire latch arm structure is enclosed in the instrument carriage and the proximal control mechanism. Therefore it is necessary to provide a mechanism for applying an outward force on the instrument latch arm 405 to release the proximal control mechanism from the instrument sterile adapter and allow removal of the surgical instrument.

Figure 10:
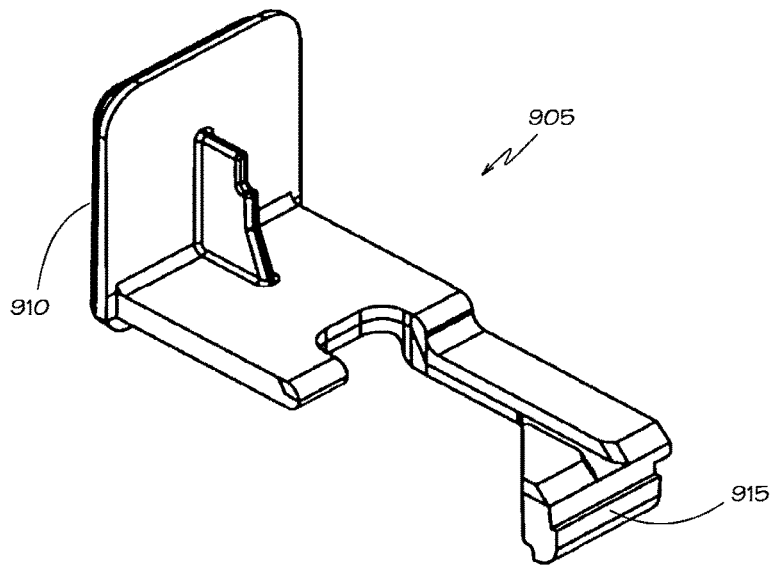
FIG. 10 is a perspective view of a latch release member.

Referring to FIG. 8D, the proximal control mechanism 240 includes a pair of latch release members 905A, 905B. FIG. 10 shows a perspective view of a single latch release member 905. Each latch release member 905 includes a button portion 910 and a latch arm engaging portion 915 that extends perpendicularly from the button portion. As can be seen in FIG. 8D, two identical latch release members 905A, 905B may be assembled opposite each other on the base of the proximal control mechanism 240. Each of the two button portions 910 is accessible on an outside surface of the proximal control mechanism 240. The two button portions 910 are on opposite outside surface of the proximal control mechanism 240 with the two latch arm engaging portions 915 extending toward the other button portion. When inward forces are applied to button portions 910 of the pair of latch release members 905A, 905B, the pair of latch release members are pushed inward and closer to each other, and the latch arm engaging portions 915A, 9158 move outward to apply an outward force on the instrument latch arms 405 to release the proximal control mechanism from the instrument sterile adapter and allow removal of the surgical instrument as shown in FIG. 9H. After the surgical instrument is removed, the instrument sterile adapter 310 may be removed from the instrument carriage 130 as described above.

Since it is necessary to provide a mechanism for applying an outward force on the instrument latch arm 405 to release the proximal control mechanism from the instrument sterile adapter and allow removal of the surgical instrument, it is desirable to provide a backup mechanism for applying an outward force on the instrument latch arm in case the primary mechanism is unavailable for any reason.

Figure 11:
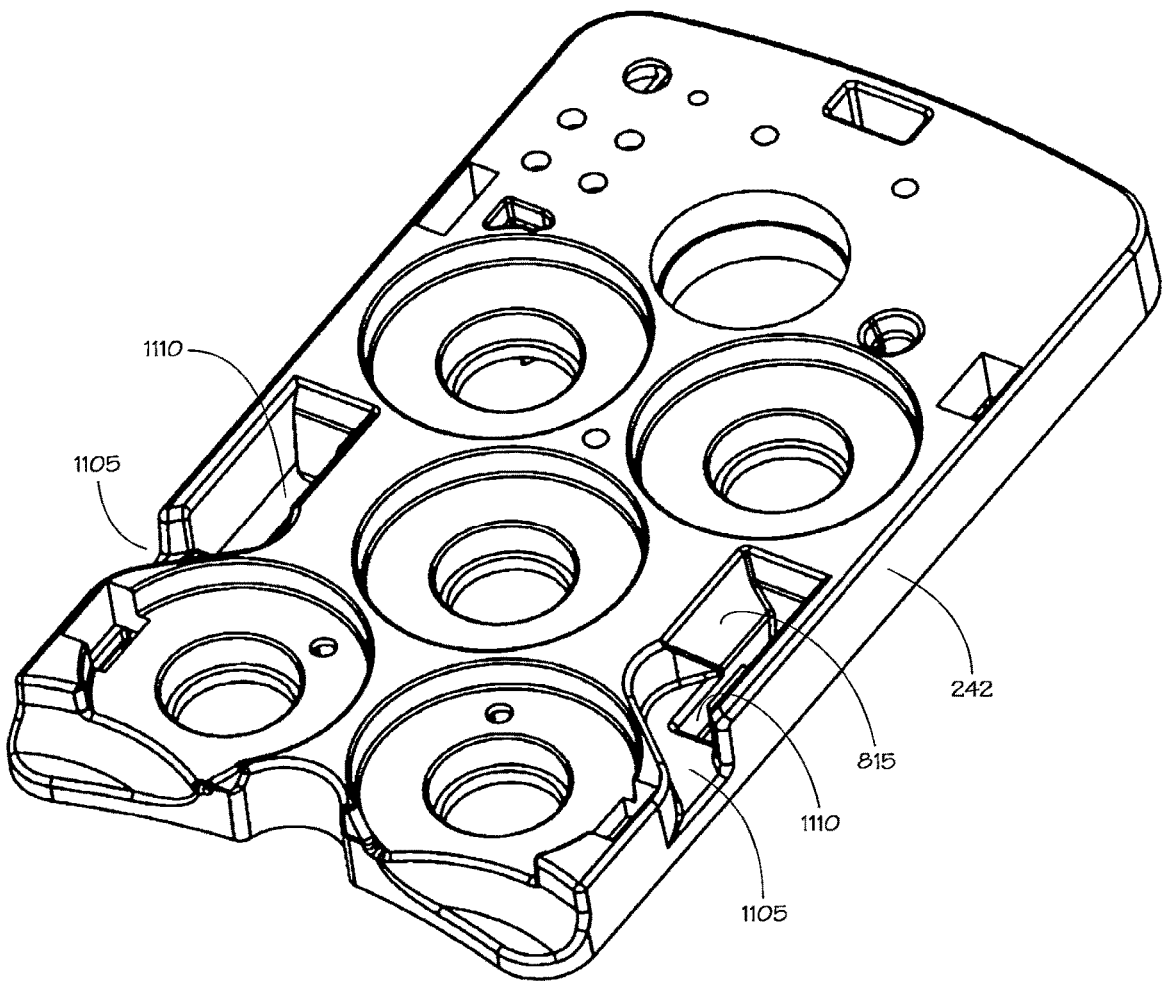
FIG. 11 is a bottom perspective view of a proximal control mechanism of a surgical instrument.

Referring to FIG. 11, a perspective view of the proximal control mechanism 240 of a surgical instrument is illustrated. The surface of the proximal control mechanism that directly engages the instrument sterile adapter is shown. Two release channels 1105 provide a backup surgical instrument release mechanism in the event that the latch release members 905 cannot be used to release the proximal control mechanism. The release channels 1105 allow a release tool access to the instrument latch arms 405 when the proximal control mechanism 240 is attached to the instrument sterile adapter. The release tool may be a rigid, slender, and elongate tool, such as an Allen wrench.

Figure 12:
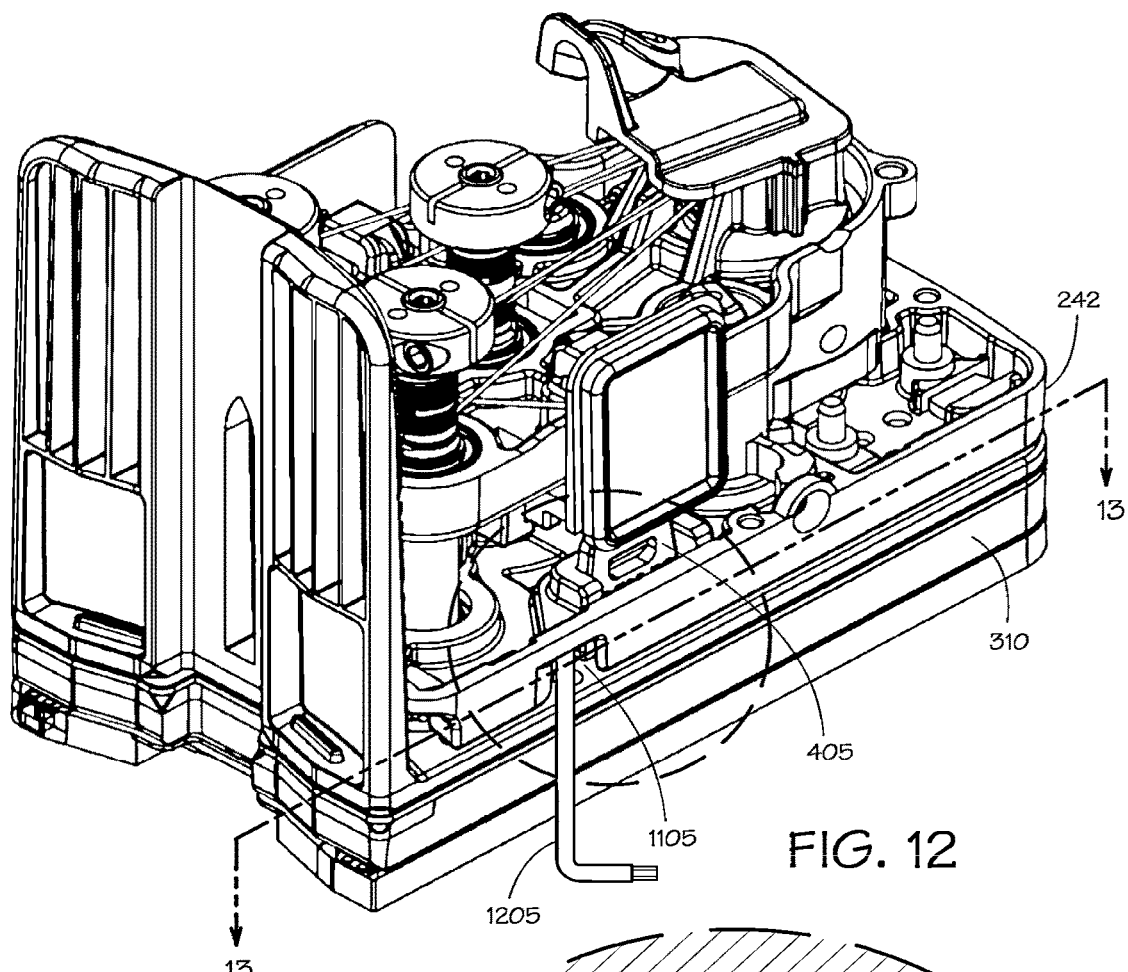
FIG. 12 is an illustration of the operation of a backup release mechanism.
Figure 13:
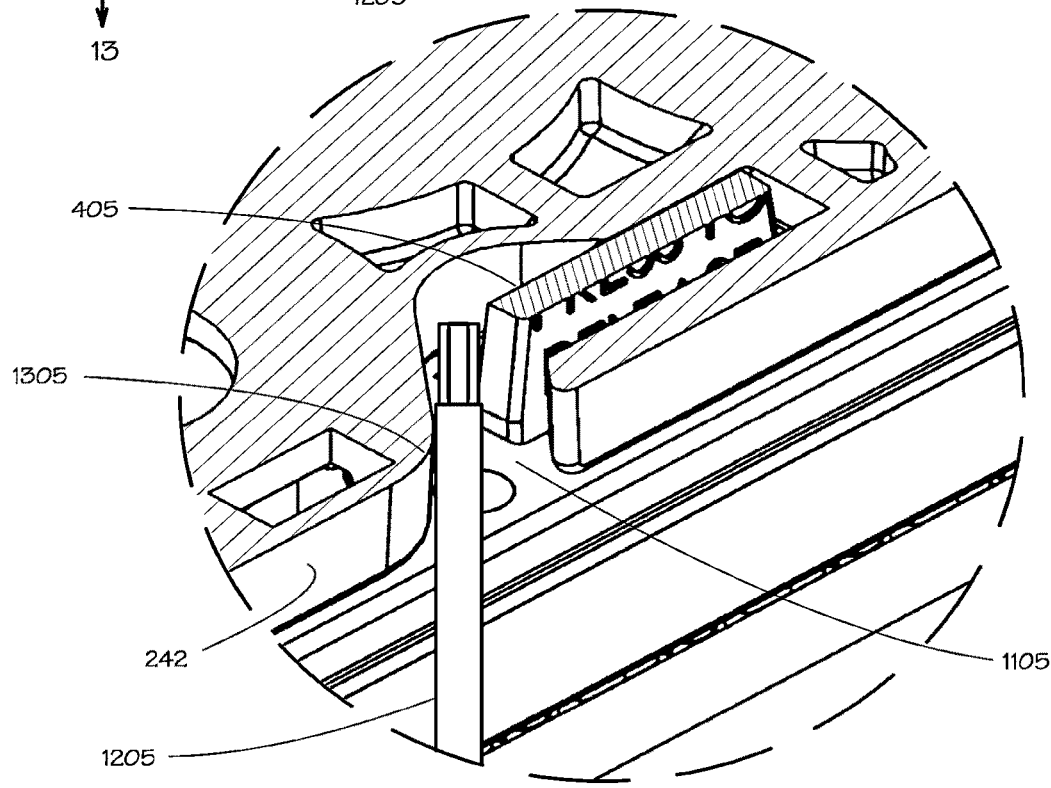
FIG. 13 is a detail view of the operation of the backup release mechanism.

Referring further to FIGS. 12 and 13, illustrations of the operation of the backup release mechanism are shown. FIG. 12 is a perspective view of a proximal control mechanism 240 of a surgical instrument attached to an instrument sterile adapter 310. FIG. 13 is detail cross-sectional of the circled portion of FIG. 12 taken along the section line 13-13.

Each of the release channels 1105 provides a passage extending from an outer periphery of the instrument control surface 242 to an opening 1110 in the instrument control surface of the proximal control mechanism 240 through which an instrument latch arm 405 enters to engage the second locking surface on the proximal control mechanism. Each of the release channels 1105 is shaped such that one may insert a release tool 1205 through the channel. An end portion of the release tool 1205 engages the inward side of the instrument latch arm 405. The release tool 1205 is used as a lever to pry outward the instrument latch arm 405 and release it from the corresponding second locking surfaces 810, with a section 1305 of the channel wall acting as the fulcrum.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

The invention claimed is:

1. A medical instrument comprising:
an instrument control surface configured to mate with an instrument sterile adapter to receive input drive forces through the instrument sterile adapter to control actuation of the medical instrument, the instrument control surface comprising an opening defined in the instrument control surface;
a latch structure comprising a locking surface configured to engage a latch arm in response to the latch arm being received in the opening, wherein, in an engaged state of the locking surface with the latch arm, the medical instrument is attached to the instrument sterile adapter and the latch structure is arranged to prevent movement of an end portion of the latch arm in a first direction; and
a latch release member that is moveable in the engaged state of the latch arm with the locking surface to exert a force causing movement of the latch arm in a second direction to disengage the latch arm from the locking surface.

2. The medical instrument of claim 1,
wherein the locking surface is configured to, in the engaged state of the locking surface with the latch arm, prevent the latch arm from being removed from the opening.

3. The medical instrument of claim 1,
wherein, in a state of the instrument sterile adapter attached to an instrument carriage and the medical instrument attached to the instrument sterile adapter, the latch structure being arranged to prevent movement of the end portion of the latch arm in the first direction prevents the instrument sterile adapter from being detached from the instrument carriage.

4. The medical instrument of claim 3,
wherein the latch arm is part of a latch plate of the instrument sterile adapter configured to engage a carriage latch structure of the instrument carriage to attach the instrument sterile adapter to the instrument carriage, and
wherein the latch structure being arranged to prevent movement of the end portion of the latch arm in the first direction prevents the latch plate from disengaging from the carriage latch structure.

5. The medical instrument of claim 1,
wherein the latch structure being arranged to prevent movement of the end portion of the latch arm in the first direction comprises the latch structure blocking the latch arm.

6. The medical instrument of claim 1,
wherein the latch structure comprises an angled lead-in surface configured to deflect the end portion of the latch arm in the second direction as the latch arm is received within the opening.

7. The medical instrument of claim 6,
wherein at least a portion of the latch structure comprising at least a portion of the angled lead-in surface and at least a portion of the locking surface protrudes into an aperture of the latch arm to engage the locking surface with the latch arm.

8. The medical instrument of claim 7,
wherein the latch release member is configured to disengage the latch arm by deflecting the end portion of the latch arm in the second direction such that the portion of the latch structure protruding into the aperture of the latch arm is removed from the aperture.

9. The medical instrument of claim 1,
wherein:
the first and second directions are transverse to a direction of insertion of the latch arm into the opening,
the first and second directions are parallel to the instrument control surface, and/or
the first direction is toward a centerline of the medical instrument and the second direction is away from the centerline.

10. The medical instrument of claim 9,
wherein the latch release member comprises a button that is depressible in the second direction.

11. A medical system comprising:
an instrument carriage;
an instrument sterile adapter removably attachable to the instrument carriage; and
a medical instrument removably attachable to the instrument sterile adapter, in an attached state of the instrument sterile adapter to the instrument carriage, to receive input drive forces from the instrument carriage through the instrument sterile adapter to control actuation of the medical instrument,
wherein the instrument sterile adapter comprises a latch plate configured to
engage a carriage latch structure of the instrument carriage to attach the instrument sterile adapter to the instrument carriage, and
engage an instrument latch structure of the medical instrument to attach the medical instrument to the instrument sterile adapter, and
wherein in an engaged state of the latch plate with the carriage latch structure and with the instrument latch structure, the medical instrument is arranged to prevent the instrument sterile adapter from being detached from the instrument carriage.

12. The medical system of claim 11,
wherein in the engaged state of the latch plate with the carriage latch structure and with the instrument latch structure, the medical instrument is arranged to prevent the latch plate from being disengaged from the carriage latch structure which prevents the instrument sterile adapter from being detached from the instrument carriage.

13. The medical system of claim 12,
wherein the latch plate comprises a first arm coupled to a second arm, the second arm configured to engage the carriage latch structure,
wherein the latch plate is disengagable from the carriage latch structure by motion of an end portion of the first arm in a first direction, and
wherein in the engaged state of the latch plate with the carriage latch structure and with the instrument latch structure, the medical instrument is arranged to prevent motion of the end portion of the first arm in the first direction which prevents the latch plate from being disengaged from the carriage latch structure.

14. The medical system of claim 13,
wherein the medical instrument being arranged to prevent motion of the end portion of the first arm in the first direction comprises the instrument latch structure blocking the first arm.

15. The medical system of claim 13,
wherein the first arm is configured to engage with the instrument latch structure.

16. The medical system of claim 15,
wherein the medical instrument comprises a latch release member moveable in the engaged state of the first arm with the instrument latch structure to disengage the first arm from the instrument latch structure by exerting a force causing movement of the end portion of the first arm in a second direction, opposite the first direction.

17. The medical system of claim 16,
wherein the latch release member comprises a button that is depressible in the second direction.

18. The medical system of claim 13,
wherein the latch plate further comprises a connecting member coupled to the first and second arms, and
wherein the connecting member is configured to, in response to motion of the end portion of the first arm in the first direction, elastically deform and cause motion of an end portion of the second arm in a second direction opposite the first direction.

19. The medical system of claim 11,
wherein in the engaged state of the latch plate with the instrument latch structure, the medical instrument being arranged to prevent the instrument sterile adapter from being detached from the instrument carriage comprises the instrument latch structure being arranged to block motion of a portion of the latch plate in a first direction.

20. The medical system of claim 11,
wherein:
the latch plate comprises latch arms and a first direction is transverse to a direction of extent of the latch arms in the engaged state of the latch plate with the carriage latch structure and with the instrument latch structure,
the medical instrument comprises an instrument control surface configured to mate with the instrument carriage and the first direction is parallel to the instrument control surface, and/or
the first direction is towards a centerline of the medical instrument.

* * * * *